(12) United States Patent
Wijbrans et al.

(10) Patent No.: US 10,094,768 B2
(45) Date of Patent: Oct. 9, 2018

(54) OPTICAL FIBER CALIBRATION CONNECTOR

(71) Applicant: KONINKLIJKE PHILIPS N.V., Eindhoven (NL)

(72) Inventors: Klaas Cornelis Jan Wijbrans, Eindhoven (NL); Gerhardus Wilhelmus Lucassen, Eindhoven (NL); Bernardus Hendrikus Wilhelmus Hendriks, Eindhoven (NL); Christian Reich, Eindhoven (NL); Johannes Antonius Van Rooij, Eindhoven (NL); Jaap Knoester, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 52 days.

(21) Appl. No.: 15/301,898

(22) PCT Filed: Apr. 7, 2015

(86) PCT No.: PCT/EP2015/057435
§ 371 (c)(1),
(2) Date: Oct. 4, 2016

(87) PCT Pub. No.: WO2015/158564
PCT Pub. Date: Oct. 22, 2015

(65) Prior Publication Data
US 2017/0108430 A1 Apr. 20, 2017

Related U.S. Application Data

(60) Provisional application No. 61/980,164, filed on Apr. 16, 2014.

(30) Foreign Application Priority Data

May 9, 2014 (EP) .................................... 14167748
Dec. 17, 2014 (EP) .................................... 14198423

(51) Int. Cl.
*G01N 21/00* (2006.01)
*G01N 21/27* (2006.01)
*G02B 6/38* (2006.01)

(52) U.S. Cl.
CPC .......... *G01N 21/276* (2013.01); *G02B 6/3825* (2013.01); *G02B 6/3845* (2013.01); *G02B 6/3866* (2013.01); *G02B 6/3885* (2013.01); *G01N 2201/084* (2013.01)

(58) Field of Classification Search
CPC ... H01J 37/32935; G01N 21/64; G01N 21/68; G01N 2015/1037; G01J 3/02
USPC .......................................................... 356/72
See application file for complete search history.

(56) References Cited

U.S. PATENT DOCUMENTS 4,050,450 A 9/1977 Polanyi
4,708,432 A 11/1987 Berg
(Continued)

FOREIGN PATENT DOCUMENTS

| EP | 1037078 A1 | 9/2000 |
|---|---|---|
| EP | 1122565 A1 | 8/2001 |
| WO | 2010024859 A1 | 3/2010 |

OTHER PUBLICATIONS

Nachabe, R. et al "Estimation of Lipid and Water Concentrations in Scattering Media with Diffuse Optical Spectroscopy from 900 to 1600 nm", Journal Biomedical Optics, vol. 15, 2010.
(Continued)

*Primary Examiner* — Md M Rahman

(57) ABSTRACT

The present invention relates to an optical fiber connector for mating a first group of one or more optical fibers (102) with one or more corresponding optical fibers in a second group of one or more optical fibers (103). The optical fiber connector includes a shutter (105), which prevents the ingress of debris into the connector, and provides an optical reference surface with which to calibrate optical fibers that
(Continued)

are inserted into the connector. The optical fiber connector finds application in the general optical fiber field, and more particularly finds application in the medical field in which it may be used to connect optical fibers in a photonic needle application.

14 Claims, 9 Drawing Sheets

(56) References Cited

U.S. PATENT DOCUMENTS

| | | | |
|---|---|---|---|
| 4,912,720 | A | 3/1990 | Springsteen |
| 7,005,623 | B2 | 2/2006 | Neuberger |
| 7,365,856 | B2 * | 4/2008 | Everett .................. A61B 3/102 |
| | | | 250/227.19 |
| 2004/0021078 | A1 * | 2/2004 | Hagler ..................... G01J 3/02 |
| | | | 250/339.13 |
| 2004/0052473 | A1 | 3/2004 | Seo |
| 2009/0073432 | A1 * | 3/2009 | Jalali ........................ G01J 3/10 |
| | | | 356/301 |

OTHER PUBLICATIONS

Farrel, T.J. et al "A diffusion theory model of spatially resolved, steady-state diffuse reflectance for the non-invasive determination of tissue optical properties", Medical Physics, vol. 19, 1992—Abstract only.

* cited by examiner

1

OPTICAL FIBER CALIBRATION CONNECTOR

CROSS-REFERENCE TO PRIOR APPLICATIONS

This application is the U.S. National Phase application under 35 U.S.C. § 371 of International Application No. PCT/EP2015/057435, filed on Apr. 7, 2015, which claims the benefit of U.S. Provisional Patent Application No. 61/980,164, filed Apr. 16, 2014, European Patent Application No. 14167748.4, filed May 9, 2014 and European Patent Application No. 14198423.7, filed on Dec. 17, 2014. These applications are hereby incorporated by reference.

FIELD OF THE INVENTION

The present invention relates to an optical fiber connector for interconnecting optical fibers. The invention also relates to the calibration of the optical path of an optical fiber. The optical fiber connector may be used in the general field of optical fibers, including the optical test and measurement field. More specifically the optical fiber connector finds application in the medical field wherein it may be used to calibrate optical fibers used in optical spectroscopy-based tissue analysis.

BACKGROUND OF THE INVENTION

Optical fibers connectors are used to terminate optical fibers. Optical fiber connectors may also be used to mechanically retain two optical fibers such that light carried by one optical fiber can couple into a corresponding optical fiber to form a light-transmitting path between them. A multitude of optical fiber connector types have been developed over the years for specific purposes including PC, SMA, LC and ST-type connectors. The well-known FC-type optical fiber connector for example offers high alignment accuracy with up to 500 mating cycles and finds application in the telecommunications field where a small misalignment between the optical fiber cores results in significant optical insertion losses.

Owing to variations in manufacturing tolerance and age-related degradation of materials, the transmittance of the optical path of an optical fiber connector may be subject to some variations. Some applications, particularly optical test and measurement applications, are highly sensitive to changes in the absolute, and/or relative transmittance of different wavelengths of light carried by optical fibers because such changes lead to errors in measured signals. The ability to calibrate the optical path of an optical fiber therefore finds importance in optical test and measurement equipment. In one exemplary application in the optical test and measurement field, a so-called photonic needle disclosed in document "Estimation of lipid and water concentrations in scattering media with diffuse optical spectroscopy from 900 to 1600 nm", J. Biomed. Opt. 15, 037015 (2010) by R. Nachabé, B. H. W. Hendriks, A. E. Desjardins, M. van der Voort, M. B. van der Mark, and H. J. C. M. Sterenborg, uses optical fibers to deliver light and perform spectral sensing measurements at the tip of a needle in order to analyze tissue that is in contact with the needle tip. In this example application an optical source and an optical measurement apparatus are housed within a console. Optical radiation generated by the optical source is transmitted to the needle tip by a delivery optical fiber where it interacts with tissue that is in contact with the needle tip. Following interaction of the light emitted by the delivery optical fiber with the tissue, return light is collected by a collection optical fiber and is conveyed to the optical measurement apparatus within the console. The optical interaction may include for example diffuse or specular reflections from the tissue, or fluorescence emission from chromophores in the tissue or the presence of a fluorescent marker in the tissue. The return light may therefore include for example diffusely or specularly reflected light, Raman scattered light, or fluorescence emission light. The tissue may subsequently be analyzed by comparing the spectral content of the light collected by the collection optical fiber with that of the light emitted by the delivery optical fiber. Owing to the sensitive nature of this spectral analysis, variations in the transmission spectrum of the optical fibers used in delivering and collecting the optical signals may confound analysis. In particular it is the relative variations in this transmission spectrum that lead to errors. Thus, it may be beneficial to measure the transmission spectrum of the delivery optical fiber and the collection optical fiber before use in order to carry out a calibration. Such a calibration may also be beneficial in calibrating against variations in the optical performance of other optical components in the optical measurement path, including spectrometers and light sources because the sensitivity, emissivity and attenuation as a function of wavelength and environmental parameters of these optical components may also vary. Thus, it may be beneficial to calibrate the entire optical path between the optical source and the optical detector in order to improve the accuracy of the analysis.

One device for calibrating a fiber optic probe such as a catheter is disclosed in U.S. Pat. No. 4,050,450. This patent discloses to use a attach a generally tubular reflecting member to the distal end of the catheter such that light delivered by a delivery optical fiber located within the catheter is reflected into a collection optical fiber within the catheter. The optical path is subsequently calibrated based on the optical reflectance of the tubular member.

Another device for calibrating the optical path of an optical fiber is disclosed in U.S. Pat. No. 7,005,623B2. This patent discloses a calibration sheath having one or more detectors on its interior surface. In use, the detectors measure a portion of the emitted radiation which is used to adjust the transmitted power in order to conform to desired treatment parameters.

However, a drawback of the additional components required by these solutions is that they complicate workflow.

SUMMARY OF THE INVENTION

It is an object of the invention to provide an optical fiber connector that allows a reliable optical path to be made between two or more optical fibers. Other aspects of the invention are described in the claims and associated figures.

In accordance with one aspect of the invention the optical fiber connector includes a body and a shutter. The body has two ports that share a common axis. A first port is at one end of the body and is configured to receive a first group of one or more optical fibers, and a second port is at the other end of the body and is configured to receive a second group of one or more optical fibers. The optical fibers are preferably received along a direction parallel with the common axis. The ports both extend along the common axis into a cavity. The cavity is disposed within the body and along the common axis between the first port and the second port. The shutter is hingeably mounted to the first port; the shutter being selectively moveable between a first state in which the shutter blocks the first port, and an open state. The shutter preferably has a planar form. The shutter has an outer surface and an opposing inner surface. The shutter is moveable between the closed state and the open state by applying a force to the outer surface of the shutter in a direction along the common axis. The shutter is preferably disposed within the cavity and is openable into the cavity by applying a force to the outer surface of the shutter in a direction towards the cavity. Alternatively the shutter may be disposed at the end of the port and be openable by applying a force to the outer surface of the shutter and away from the cavity. A lever may be used to facilitate application of the desired force.

The connector may thus be used to mate a first group of one or more optical fibers, with one or more corresponding optical fibers in a second group of one or more optical fibers. Consequently an optical path may be formed between corresponding optical fibers in the first and second groups. The shutter prevents debris such as dust and sand from entering the connector, which if present in an optical connector would otherwise degrade the lifetime of the connector due to abrasion of the mating optical fiber cores. Furthermore, since the first port is accessed by applying a force to the outer surface of the shutter; the shutter can be opened with the insertion force of the first group of one or more optical fibers as it is inserted into the port. The simplified insertion mechanism facilitates insertion of the first group with a single hand, thereby improving workflow. Furthermore, when a second group of one or more optical fibers is received within the second port, the orientation of the shutter respective the second group and the inherent non-zero reflectance of the inner surface permits the use of the inner surface as an optical reference surface for use in calibrating the second group of one or more optical fibers.

In accordance with another aspect of the invention the inner surface of the shutter has a predetermined optical signature within at least a first calibration wavelength interval, wherein the predetermined optical signature is selected from the group: a diffuse reflectance spectrum, a specular reflectance spectrum, a Raman scattering spectrum, a fluorescence emission spectrum. Any of these predetermined optical signatures, or a combination thereof, may advantageously be used to calibrate the optical transmission of one or more optical fibers in a second group when inserted into the second port.

In accordance with another aspect of the invention the optical fiber connector includes mechanically resistive means, the mechanically resistive means being in mechanical communication with the shutter and the body. The mechanically resistive means ensures that the shutter remains reliably closed in the closed state when the first port is unoccupied.

In accordance with another aspect of the invention both the body and the shutter of the optical fiber connector are opaque to optical wavelengths within at least a first calibration wavelength interval. Furthermore the shutter blocks the first port in the closed state to form a light-impermeable barrier between the first port and the cavity. A connector is thereby provided which can be used to perform a detector dark current calibration procedure for an optical detector which is in optical communication with an optical fiber that occupies the second port.

In accordance with another aspect of the invention the optical fiber connector includes a debris collection zone. Advantageously, any dust or sand or particles that enter into the cavity become trapped at the debris collection zone where they are immobilized, thereby preventing abrasion of the mating surfaces of the optical fiber cores.

In accordance with another aspect of the invention an optical fiber connector arrangement is disclosed. The arrangement includes an optical fiber connector and a second group of one or more optical fibers; the second group of one or more optical fibers being received within the second port such that when delivery light emitted by the one or more optical fibers in the second group into the cavity is incident upon the inner surface of the shutter in the closed state, return light that is scattered or reflected or emitted by the inner surface of the shutter consequent to the emitted delivery light is at least partially collected by the one or more optical fibers in the second group. Such an arrangement may advantageously be used to calibrate the transmission of the optical path of the one or more optical fibers in the second group. Preferably the return light power that is collected by the one or more optical fibers in the second group consequent to the emitted delivery light is 0.1% or more, or 1% or more, or 5% or more, or 10% or more, or 20% or more or 50% or more of the delivery light power.

In accordance with another aspect of the invention another optical fiber connector arrangement is disclosed. In this arrangement the shutter of the optical fiber connector is in the open state, and the optical fiber connector arrangement includes a first group of one or more optical fibers. The first group is received within the first port such that the first group at least partially fills the cavity. Furthermore the first group is arranged respective the second group such that each optical fiber in the first group is in optical communication with one or more corresponding optical fibers in the second group. The shutter, being openable by applying a force to the outer surface of the shutter in a direction along the common axis allows the conversion of the connector between a closed state in which any one of dust or light is prevented from entering into the connector, or in which an optical calibration or dark measurement can be carried out, and a connected state in which optical communication between corresponding optical fibers in the first and second groups is achieved.

In accordance with another aspect of the invention another optical fiber connector arrangement is disclosed. This arrangement includes an optical fiber connector having a second group of one or more optical fibers inserted into the second port, an optical source and a spectrometer. The second group includes a second group delivery optical fiber and a second group return optical fiber. Furthermore the second group delivery optical fiber is in optical communication with the optical source and the second group return optical fiber is in optical communication with the spectrometer. The shutter is in the closed state such that the second group delivery optical fiber and the second group return optical fiber form an optical path between the source and the spectrometer that includes the inner surface of the shutter. Thus, the arrangement defines a configuration in which the inner surface of the shutter may be used as an optical reference surface with which to calibrate the optical transmission of the second group delivery optical fiber and the second group return optical fiber, based on the optical properties of the inner surface.

In accordance with another aspect of the invention another optical fiber connector arrangement is disclosed. This arrangement includes an optical fiber connector having a first group of one or more optical fibers inserted into the first port, and a second group of one or more optical fibers inserted into the second port. An optical source, a spectrometer and an optical probe are also included in the arrangement. The first group includes a first group delivery optical fiber and a first group return optical fiber, and the second group includes a second group delivery optical fiber and a second group return optical fiber. The first group delivery optical fiber and the first group return optical fiber each have a distal end located at the distal end of the optical probe. Furthermore, the second group delivery optical fiber and the first group delivery optical fiber form an optical path between the optical source and the distal end of the optical probe. Also, the first group return optical fiber and the second group return optical fiber form an optical path between the distal end of the optical probe and the spectrometer. The arrangement may be used to perform optical measurements at the distal end of the optical probe.

In accordance with another aspect of the invention another optical fiber connector arrangement is disclosed. This arrangement includes a connector having a first group of one or more optical fibers inserted into the first port and a second group of one or more optical fibers inserted into the second port. The first group is arranged respective the second group such that each optical fiber in the first group is in optical communication with one or more corresponding optical fibers in the second group. The first group includes a first group delivery optical fiber and a first group return optical fiber, and the second group includes a second group delivery optical fiber and a second group return optical fiber. Moreover, at least one of the following is true i) the second group delivery optical fiber (1031) has a numerical aperture (NA2D) that exceeds the first group delivery optical fiber (1035) numerical aperture (NA1D), or ii) the second group delivery optical fiber (1031) has a core diameter (D2D) that exceeds the first group delivery optical fiber (1035) core diameter (D1D), or iii) the second group return optical fiber (1032) has a numerical aperture (NA2R) that exceeds the first group return optical fiber (1036) numerical aperture (NA1R), or iv) the second group return optical fiber (1032) has core diameter (D2R) that exceeds the first group return optical fiber (1036) core diameter (D1R). By arranging that the cone angle of at least one optical fiber in the connector on the second group side, exceeds that of a corresponding optical fiber on the first group side with which it communicates, the alignment tolerance of the first group respective the second group is relaxed. By the term "exceeds" it is meant here that the ratio of the two parameters is preferably 1.1 or more, or 1.2 or more, or 1.5 or more. In accordance with another aspect of the invention a method of calibrating an optical fiber path is disclosed. The method may for example calibrate the transmission of the optical path. The method includes the steps of: measuring a reference optical spectrum (S1) with the spectrometer in the optical fiber connector arrangement of claim 10; measuring a signal optical spectrum (S2) with the spectrometer in the optical fiber connector arrangement of claim 11; and computing an adjusted optical spectrum (S3) based on either: i) the difference between the reference optical spectrum (S1) and the signal optical spectrum (S2), or ii) the ratio between the reference optical spectrum (S1) and the signal optical spectrum (S2), at one or more optical wavelengths within the spectral range detected by the spectrometer. The method may advantageously be used to calibrate the first group of one or more optical fibers using the inner surface of the shutter as an optical reference surface, and to correct a subsequently measured signal optical spectrum that is measured with an optical probe. In accordance with another aspect of the invention a computer program or computer program product is disclosed. This comprises instructions which when executed on a computer cause the computer to generate either: i) a reference optical spectrum with the optical fiber connector arrangement of claim 10, or to ii) to generate a signal optical spectrum (S2) with the spectrometer in the optical fiber connector arrangement of claim 11. The computer program or computer program product thus permits the automatic acquisition of a spectrum based on the closed or open status of the shutter.

In accordance with another aspect of the invention another computer program or computer program product is disclosed. This comprises instructions which when executed on a computer cause the computer to determine, based on the predetermined optical signature of the mating surface of first group of one or more optical fibers, or of the mating surface of a ferrule supporting the first group of one or more optical fibers, which type of first group of one or more optical fibers from a plurality of types of first group of one or more optical fibers associated with a predetermined optical signature, is in the cavity of the optical fiber connector. A lookup table may store the association between each type of first group of one or more optical fibers and its predetermined optical signature. The lookup table may be consulted during the determination process.

In accordance with another aspect of the invention another computer program or computer program product is disclosed. This comprises instructions which when executed on a computer cause the computer to perform the following steps: identify, based on the predetermined optical signature of the inner surface of the shutter, whether the shutter of the optical connector arrangement of claim 10 is in the closed state; measure a reference optical spectrum (S1) with the spectrometer in the optical fiber connector arrangement of claim 10 when the shutter is in the closed state; identify, based on the predetermined optical signature of the inner surface of the shutter, whether the shutter of the optical connector arrangement of claim 11 is in the open state; and to measure a signal optical spectrum (S2) with the spectrometer in the optical fiber connector arrangement of claim 11 when the shutter is in the open state; and to compute an adjusted optical spectrum (S3) based on either: i) the difference between the reference optical spectrum (S1) and the signal optical spectrum (S2), or ii) the ratio between the reference optical spectrum (S1) and the signal optical spectrum (S2) at one or more optical wavelengths within the spectral range detected by the spectrometer; wherein each of the above steps are performed in relation to the same optical fiber connector. The computer program or computer program product may thus advantageously automatically measure a reference spectrum and a signal optical spectrum based on the closed or open status of the shutter, and to use the reference spectrum to re-compute the signal optical spectrum, thereby improving the accuracy of the measured spectrum.

In accordance with another aspect of the invention various configurations of optical fiber connectors having corresponding alignment holes and alignment pins are provided which facilitate the mating of optical fiber connectors with improved reliability.

DETAILED DESCRIPTION OF THE INVENTION

The following description of an optical fiber connector makes reference to its use in the medical field. Particular reference is made to its use in low-cost disposable connector applications, however it is to be further appreciated that the invention also finds application in the interconnection of optical fibers in the general optical fiber application field.

In order to provide a reliable optical transmission path between a first group of one or more optical fibers, and one or more corresponding optical fibers in a second group of one or more optical fibers, an optical fiber connector is provided. The optical fiber connector has a body and a shutter. The body has a first port that is suitable for receiving the first group of one or more optical fibers, a second port that is suitable for receiving the second group of one or more optical fibers, and a cavity disposed between the first port and the second port. The first port shares a common axis with the second port. The shutter is disposed within the cavity and is hingeably mounted to the first port; the shutter being selectively movable between a closed state in which the shutter blocks the first port and in which the shutter lies in a plane that transversely intersects the common axis, and an open state in which the shutter lies in a plane that forms an acute angle with the common axis. Furthermore, the shutter has an inner surface that is innermost to the cavity, and an opposing outer surface, and the shutter is movable between the closed state and the open state by applying a force to the outer surface of the shutter in a direction along the common axis.

Figure 1:
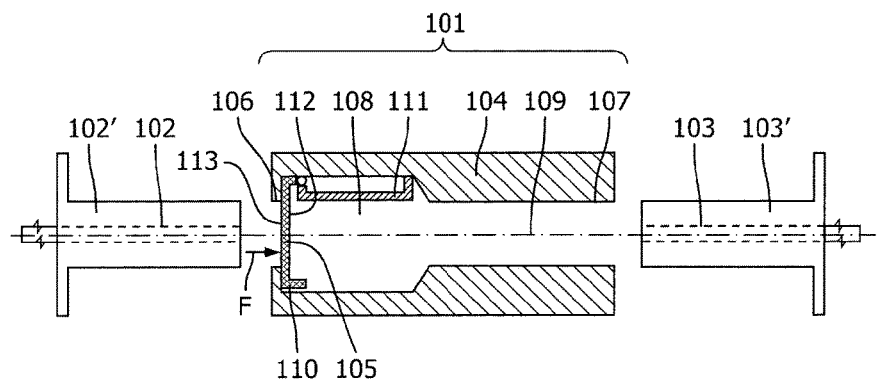
FIG. 1 illustrates an optical fiber connector 101 having a shutter 105, and a separate first group of one or more optical fibers 102 and a separate second group of one or more optical fibers 103.

FIG. 1 illustrates an optical fiber connector 101 with a shutter 105, and a separate first group of one or more optical fibers 102 and a separate second group of one or more optical fibers 103. With reference to the exemplary embodiment of FIG. 1, the connector 101 may thus be used to mate the first group of one or more optical fibers 102, with one or more corresponding optical fibers in the second group of one or more optical fibers 103. The separate groups of optical fibers may be supported by respective ferrules 102', 103'. Consequently an optical path may be formed between corresponding optical fibers in the first and second groups. Shutter 105 is illustrated in the closed state in dark shading as item 110 and in an open state in hatched shading as item 111. Shutter 105 prevents debris such as dust and sand from entering the connector, which if present in an optical connector would otherwise degrade the lifetime of the connector due to abrasion of the mating optical fiber cores. Furthermore, since the first port 106 is accessed by applying a force, labeled as item F, to the outer surface 113 of the shutter 105; the shutter can be opened with the force of the first group of one or more optical fibers 102 as it is inserted into the first port 106. The simplified insertion mechanism facilitates insertion of the first group with a single hand, thereby improving workflow.

Whilst in FIG. 1 a connector with a single shutter 105 is illustrated, it is to be appreciated that the connector may alternatively have an additional second shutter that is likewise hingeably mounted to the second port to offer the same advantages, and furthermore has bidirectional functionality. Suitable shutter and body materials include plastics, ceramics and metals.

An optical fiber is inherently able to deliver light to, and at the same time is also inherently sensitive to light within, a predetermined cone of angles, the cone being aligned axially with the end of the optical fiber. This cone of angles is determined by the numerical aperture, NA, of the optical fiber. An optical fiber with a low NA delivers light to, and is sensitive to, light within a narrow angular range, thus a narrow cone angle, whereas higher NA optical fibers are associated with a larger cone angle. In any event an optical fiber delivers light to and is sensitive to light that is aligned with the optical fiber's axis. With reference to FIG. 1, when a second group of optical fibers 103 is received within the second port 107 of the connector 101 and the shutter 105 is in the closed state 110, the second group of optical fibers 103 faces the inner surface 112 of the shutter 105. This is because in the closed state 110, shutter 105 lies in a plane that transversely intersects common axis 109. Consequently at least some of the radiation, i.e. UV, visible or infrared light emitted by an optical fiber in the second group 103 will be incident on the inner surface 112 of the shutter 105, and at least some of this light will subsequently collected by the same, or another optical fiber in the second group 103. Preferably the shutter lies in a plane that perpendicularly intersects the common axis, but providing this intersection is within approximately 5 degrees either side of perpendicular, substantially the same effect will be achieved. In one configuration the inner surface of the shutter has non-zero reflectance within at least a first calibration wavelength interval; a situation which is satisfied by almost all practical materials. Desirably the reflectance of the inner surface exceeds 1%, or exceeds 10%, or exceeds 50%, at a predetermined wavelength within at least a first calibration wavelength interval. The calibration wavelength interval may for example be the visible spectrum, the infrared spectrum, or the UV spectrum, or any combination thereof. Consequently the inner surface 112 of the shutter 105 inherently allows optical fiber connector 101 to be used to calibrate the transmission of an optical fiber. In order to perform the calibration a second group of one or more optical fibers 103 should be inserted into the second port 107 of connector 101 in FIG. 1 and the shutter should be in the closed state. At least one optical fiber within the second group 103 should deliver radiation, i.e. UV, visible or infrared light into cavity 108, and the light collected by the at least one optical fiber within the second group 103 should be detected, for example using a spectrometer, or an optical detector. The amount, or the spectrum of the light coupled into the delivery optical fiber may then be compared to that returned by the collecting optical fiber in order to calibrate the optical path.

In so doing the shutter 105 of the optical fiber connector 101 serves both to prevent the ingress of debris, and facilitates an optical calibration procedure without the need for a separate optical reference surface such as the prior art calibration cap. The ability to re-use the same inner surface of the shutter as an optical calibration surface for consecutive calibration procedures is advantageous furthermore because it permits successive calibrations with the same optical reference surface. This effect is not achieved by the prior art calibration cap, which is typically discarded following a single use. Thus a more reliable calibration procedure is achieved by using the inner surface of the shutter as an optical calibration surface.

With reference to FIG. 1, preferably the inner surface 112 of the shutter 105 has a predetermined optical signature within at least a first calibration wavelength interval, wherein the predetermined optical signature is selected from the group: a diffuse reflectance spectrum, a specular reflectance spectrum, a Raman scattering spectrum, a fluorescence emission spectrum. As described above, any of these predetermined optical signatures, or a combination thereof, may advantageously be used to calibrate the optical transmission of one or more optical fibers in second group 103 when inserted into second port 107. This may be achieved by comparing the amount, or the spectrum of the light coupled into the delivery optical fiber with that returned by the collecting optical fiber, and based on the predetermined optical signature. As described above, this advantageously leads to a reliable calibration procedure because the same inner surface of the shutter is used for each calibration procedure. The calibration wavelength interval may be within the ultraviolet, the visible or infrared spectral range and is desirably within the spectrum of wavelengths transmitted by the second group of one or more optical fibers. The calibration wavelength interval may be single broad band of optical wavelengths, such as for example from 300 nm to 2000 nm, from 400 nm to 1700 nm, or from 400 nm to 800 nm; or one or more narrow bands with a wavelength interval of for example 100 nm, or 50 nm, or 10 nm. A single broad band permits a calibration to be performed over a broad range of wavelengths, whilst a narrower band may provide a predetermined optical signature only within a specific narrow group of wavelengths.

A diffuse reflectance spectrum may be provided by a scattering surface. Examples of suitable scattering surfaces include PolyTetraFluoroEthylene, PTFE, ground glass, or roughened plastic surfaces. Preferably the surface provides a Lambertian reflectance profile. A suitable commercially-available material for providing a diffuse reflectance spectrum that includes PTFE is described in U.S. Pat. No. 4,912,720 and sold under the trademark SPECTRALON by Labsphere, Inc., North Sutton, N.H. This material is known to provide an excellent diffuse reflection spectrum with which the desired optical path calibration can be made. For both Spectralon and PTFE, a layer thickness of preferably 5 mm or more should be used in order to provide repeatable diffuse reflectance measurements.

A specular reflectance spectrum may be provided by a polished surface, such as a polished metal layer, for example a chrome, silver or gold layer, or a polished plastic or glass surface. BK7 glass, for example is known to have a reflectance of approximately 4% across a substantial part of the visible wavelength range. Multilayer optical coatings may also be used to generate the desired specular reflectance spectrum. The multilayer coating may furthermore be designed to have a predetermined reflectance within a single broad band, or at one or more narrower bands. In one example implementation the multilayer optical coating may be designed to have a specific reflectance such as 50% to red wavelengths, and another specific reflectance such as 10% to green wavelengths. In so doing a calibration optical surface may be provided which tests different parts of the optical spectrum at different points within the dynamic range of an optical detector. A coating formed by the process of nano-imprint lithography is also suitable for providing the desired specular reflectance spectrum.

A Raman scattering spectrum is inherent in many materials and is unique to a particular material. A powder coating may be used to provide an enhanced Raman scattering spectrum having a larger reflectance signal. A Raman scattering spectrum may be detected by using a laser optical source to irradiate a surface, such as the inner surface of the shutter, and collecting the scattered light on an optical detector. The scattered light that is close in wavelength to the optical source wavelengths is typically indicative of Rayleigh scattering and is filtered out.

A fluorescence emission spectrum may be provided by including a layer of fluorescent material on the inner surface of the shutter. Alternatively the shutter may be formed from a plastic having a having a fluorescent dye incorporated therein. A fluorescence emission spectrum may be particularly suited to calibrating the optical path in fluorescence applications.

The predetermined optical signature may furthermore be used to determine whether the shutter is in the open state or in the closed state. With reference to FIG. 1, this may be achieved by comparing the amount, or the spectrum of the light that is coupled into a delivery optical fiber within second group 103 when it is inserted into second port 107, to that returned by a collecting optical fiber within second group 103. When the shutter is in the closed state a predictable signal based on the predetermined optical signature will be detected, whereas any deviation from this predicted signal is indicative of the shutter being in the open state. This may subsequently be used as part of an automatic calibration procedure, wherein a method routine executed by a computer is configured to perform a calibration procedure with the shutter in the closed state, and is configured to perform an optical signal measurement procedure when the shutter is in the open state. In one example configuration the inner surface of the shutter may have a predetermined reflectance value for red optical wavelengths. Thus, the closed state may be determined by measuring the signal returned by the collecting optical fiber with an optical detector or a spectrometer, the closed state being confirmed when the reflectance of red optical wavelengths corresponds to that expected from the predetermined reflectance value. The same effect may be achieved by using a fluorescent, or a diffuse reflecting coating on the inner surface of the shutter.

The predetermined optical signature may furthermore be associated with a particular type of connector. Consequently by comparing the amount, or the spectrum of the light coupled into the delivery optical fiber, to that returned by the collecting optical fiber, and based on the predetermined optical signature, the particular type of connector that is connected to an optical fiber may be determined. In one example configuration this may be achieved by ensuring that the inner surface of the shutter has, for example have a predetermined reflectance at red and at green optical wavelengths, the particular ratio of the red reflectance to the green reflectance being indicative of a particular connector type. Thus, an optical detector or optical analyzer such as a spectrometer may be used to analyze the return light in order to determine which specific connector selected from a plurality of optical connectors each having an associated predetermined reflectance, is connected to an optical fiber.

Likewise, the predetermined optical signature may furthermore be associated with a particular type of first group of one or more optical fibers. By arranging that at least a portion of the mating surface of the first group of one or more optical fibers, or that the mating surface of the ferrule supporting the first group, has a predetermined optical signature as described above, the predetermined optical signature being associated with a specific type of ferrule or a specific type of first group of one or more optical fibers, the same technique can be used to identify which first group from of a plurality of first groups of optical fibers are being inserted into the connector. This can be achieved by measuring or analyzing the return light as described above during insertion of the first group into the first port.

Preferably both the body 104 and the shutter 105 of the optical fiber connector 101 in FIG. 1 are opaque to optical wavelengths within the at least a first calibration wavelength interval. Furthermore the shutter 105 preferably blocks the first port 106 in the closed state 110 to form a light-impermeable barrier between the first port 106 and the cavity 108. Thus, a connector is provided which is suitable for performing a detector dark current calibration procedure for an optical detector which is in optical communication with an optical fiber within the second group 103 when occupies the second port 107. The ability to perform a detector dark current calibration is advantageous in optical test and calibration instruments as it allows a baseline offset signal that is generated by the detector dark current to be subtracted from a measured optical signal. This finds particular application in spectral tissue sensing applications, permitting a baseline dark spectrum to be subtracted from subsequently measured spectra, thereby improving the subsequent analysis of the tissue type. Suitable materials for the body and the shutter include plastics and metals.

Figure 2:
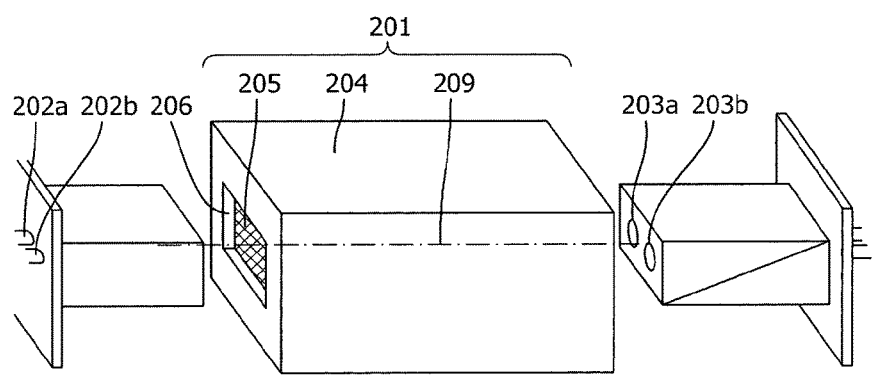
FIG. 2 illustrates a perspective view of an optical fiber connector 201 having a shutter 205.

FIG. 2 illustrates a perspective view of an optical fiber connector 201 having a shutter 205. Optical fiber connector 201 has a common axis 209 which is shared by first port 206 and a second port, not shown. Shutter 205 is shown in the closed state. Connector 201 may be used to make optical communication between optical fiber 202a in a first group of two optical fibers 202a, 202b, and corresponding optical fiber 203a in a second group of two optical fibers 203a, 203b. Optical fibers 202b and 203b may likewise be connected with optical fiber connector 201.

Figure 3:
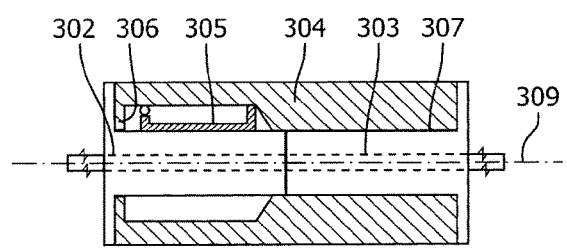
FIG. 3 illustrates an optical fiber connector having a shutter 305 in the open state with a first group of one or more optical fibers 302 received within a first port 306 of the connector and a second group of one or more optical fibers 303 received within a second port 307 of the connector.

FIG. 3 illustrates an optical fiber connector having a shutter 305 in the open state with a first group of one or more optical fibers 302 received within a first port 306 of the connector and a second group of one or more optical fibers 303 received within a second port 307 of the connector. First port 306 and second port 307 share a common axis 309. In so doing, an optical path is formed between corresponding optical fibers in the first group 302 and the second group 303. In FIG. 3 the coupling faces of the corresponding optical fibers are shown as touching, however, in some configurations it is contemplated to separate corresponding optical fibers with an air gap or a positive lens, such as a ball lens, in order to relax the alignment tolerance requirements for the optical fibers.

Figure 4:
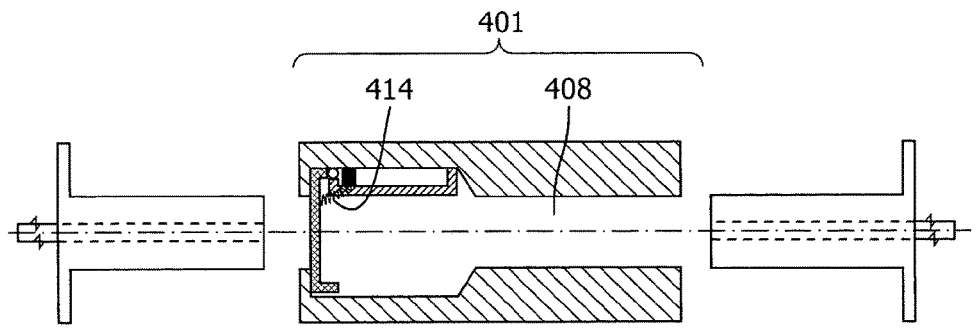
FIG. 4 illustrates an optical fiber connector 401 having mechanically resistive means 414 configured to provide a restoring force to counteract movement of the shutter from the closed state towards the open state.
Figure 4A:
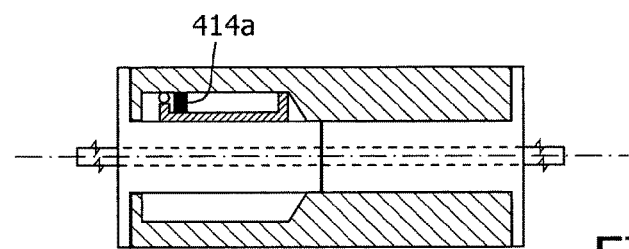
FIG. 4A illustrates an optical fiber connector having a shutter in the open state, with a first group of optical fibers received within a first port of the connector and a second group of optical fibers received within a second port of the connector, together with mechanically resistive means 414a configured to provide a restoring force to counteract movement of the shutter from the closed state towards the open state.

FIG. 4 illustrates an optical fiber connector 401 having mechanically resistive means 414 configured to provide a restoring force to counteract movement of the shutter from the closed state towards the open state. Thus in the absence of any additional forces the shutter is held in the closed state. FIG. 4A illustrates an optical fiber connector having a shutter in the open state, with a first group of optical fibers received within a first port of the connector and a second group of optical fibers received within a second port of the connector, together with mechanically resistive means 414a configured to provide a restoring force to counteract movement of the shutter from the closed state towards the open state. The mechanically resistive means 414, 414a is in mechanical communication with the shutter and the body in FIGS. 4, 4A. The mechanically resistive means, which may for example be a spring, a compressive member such as a rubber rod, an elastic or rubber band, an elastically deformable blade, or indeed any deformable member configured to provide a restoring force, is configured to provide a restoring force to the shutter to prevent movement of the shutter between the closed state and the open state. In so doing the mechanically resistive means ensures that the shutter remains reliably closed in the closed state when the first port is unoccupied. This further improves the reliability of the shutter at preventing the ingress of debris, and reliably keeps the shutter in the desired closed state during an optical calibration procedure.

Figure 5:
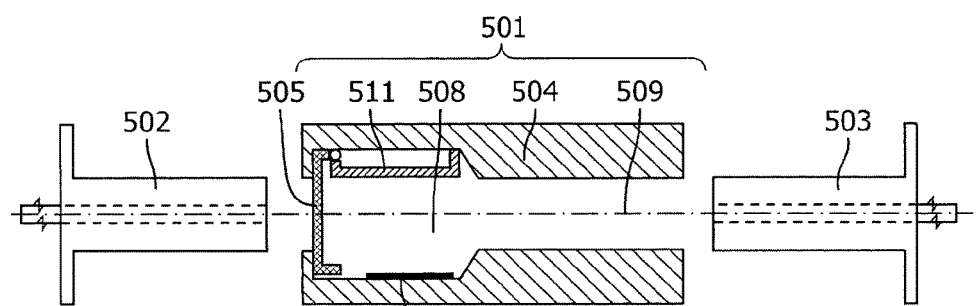
FIG. 5 illustrates an optical fiber connector 501 having a debris collection zone 515.
Figure 5A:
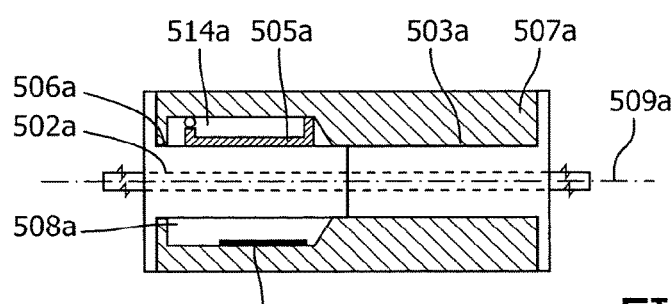
FIG. 5A illustrates an optical fiber connector having a debris collection zone 515a wherein the connector has a first group of optical fibers 502a received within a first port 506a of the connector and a second group of optical fibers 503a received within a second port 507a of the connector.

FIG. 5 illustrates an optical fiber connector 501 having a debris collection zone 515. FIG. 5A illustrates an optical fiber connector having a debris collection zone 515a wherein the connector has a first group of optical fibers 502a received within a first port 506a of the connector and a second group of optical fibers 503a received within a second port 507a of the connector. Debris collection zone 515, 515a is within the cavity 508, 508a respectively, and is formed from either a sticky surface or an electrostatically charged surface. Advantageously, any dust or sand or particulates that enter the cavity become trapped at the debris collection zone where they are immobilized. The lifespan of the connector is thereby improved because debris is prevented from abrading the optical mating surfaces of optical fibers mated by the connector. In particular the number of connector mating cycles is improved in this way.

Figure 6:
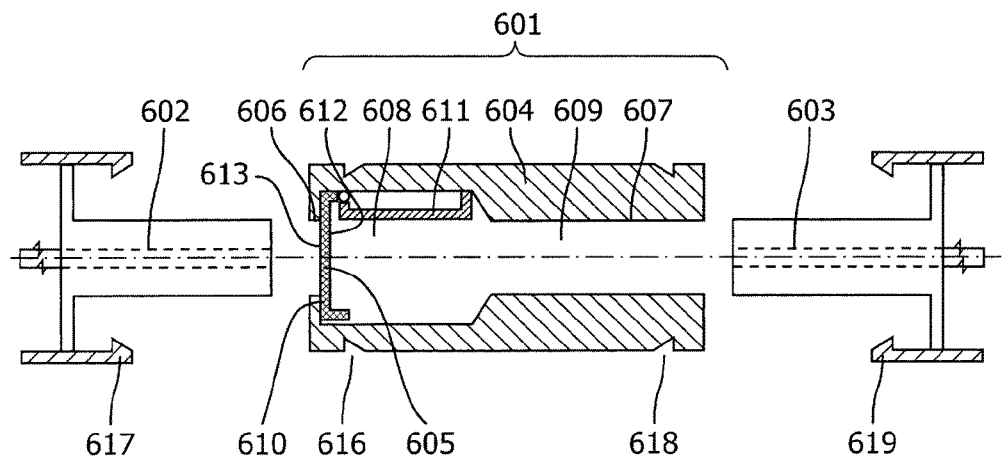
FIG. 6 illustrates an optical fiber connector 601 having first retaining means 616 for retaining a first group 602 of one or more optical fibers in a first port 606 of the connector 601 and second retaining means 618 for retaining a second group 603 of optical fibers in a second port 607 of the connector 601.
Figure 6A:
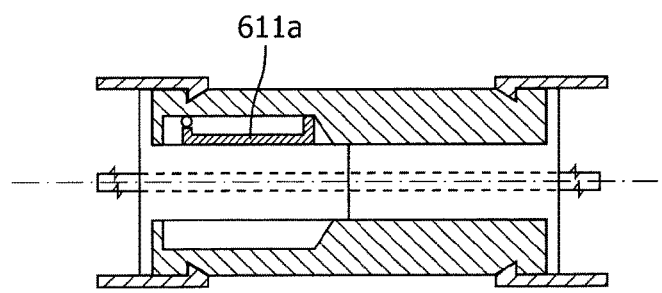
FIG. 6A illustrates an optical fiber connector having first and second retaining means wherein the connector has a first group of optical fibers received within a first port of the connector and a second group of optical fibers received within a second port of the connector.

FIG. 6 illustrates an optical fiber connector 601 having first retaining means 616 for retaining a first group 602 of one or more optical fibers in a first port 606 of the connector 601 and second retaining means 618 for retaining a second group 603 of optical fibers in a second port 607 of the connector 601. Shutter 605 is in the closed state 610. FIG. 6A illustrates an optical fiber connector having first and second retaining means wherein the connector has a first group of optical fibers received within a first port of the connector and a second group of optical fibers received within a second port of the connector. The shutter is in the open state 611a. Whilst the exemplary retaining means shown is a snap-connection retaining means, it may alternatively be provided by for example a friction fit, a screwthread, or a bayonet fitting.

Figure 7:
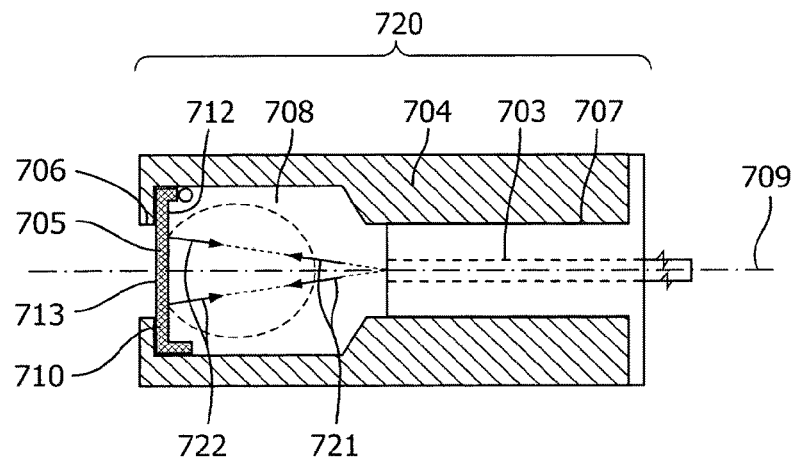
FIG. 7 illustrates an optical fiber connector arrangement 720 comprising an optical fiber connector and a second group of optical fibers 703 received within a second port 707 of the connector, wherein the shutter 705 of the connector is in the closed state 710.

FIG. 7 illustrates an optical fiber connector arrangement 720 comprising an optical fiber connector and a second group of optical fibers 703 received within a second port 707 of the connector, wherein the shutter 705 of the connector is in the closed state 710. In FIG. 7 the second group of one or more optical fibers 703 is received within the second port 707 such that when delivery light 721 emitted by the one or more optical fibers in the second group 703 into the cavity 708 is incident upon the inner surface 712 of the shutter 705 in the closed state 710, return light 722 that is scattered or reflected or emitted by the inner surface 712 of the shutter 705 consequent to the emitted delivery light is at least partially collected by the one or more optical fibers in the second group 703. Such an arrangement may advantageously be used to calibrate the transmission of the optical path of the one or more optical fibers in the second group 703. Such an arrangement may furthermore be used to perform a dark calibration of an optical detector connected to an optical fiber within the second group 703 of optical fibers by arranging that the body 704 and the shutter 705 are opaque to optical wavelengths within at least a first calibration wavelength interval, and by arranging that the shutter 705 blocks the first port 706 in the closed state 710 to form a light-impermeable barrier between the first port 706 and the cavity 708.

Figure 8:
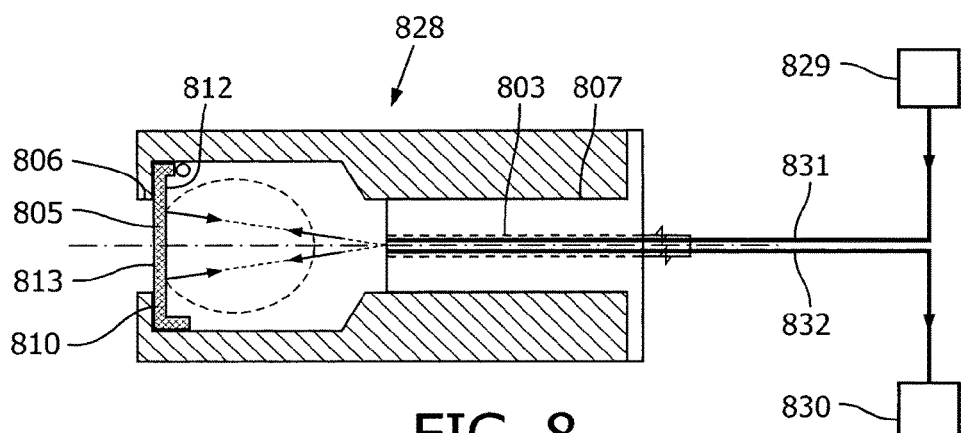
FIG. 8 illustrates an optical fiber connector arrangement 828 comprising an optical fiber connector, a second group of optical fibers 803 received within the second port 807 of the connector, an optical source 829 and a spectrometer 830, wherein the shutter 805 of the connector is in the closed state 810.

FIG. 8 illustrates an optical fiber connector arrangement 828 comprising an optical fiber connector, a second group of optical fibers 803 received within the second port 807 of the connector, an optical source 829 and a spectrometer 830, wherein the shutter 805 of the connector is in the closed state 810. The second group 803 includes a second group delivery optical fiber 831 and a second group return optical fiber 832. Furthermore the second group delivery optical fiber 831 is in optical communication with the optical source 829 and the second group return optical fiber 832 is in optical communication with the spectrometer 830. The shutter 805 is in the closed state 810 such that the second group delivery optical fiber 831 and the second group return optical fiber 832 form an optical path between the source 829 and the spectrometer 830 that includes the inner surface 812 of the shutter 805. Thus, the inner surface of the shutter faces the distal ends of both the second group delivery optical fiber 831 and the second group return optical fiber 832. Thus, the arrangement defines a configuration in which the inner surface of the shutter may be used as an optical reference surface with which to calibrate the optical transmission of the second group delivery optical fiber and the second group return optical fiber, based on the optical properties of the inner surface. Suitable spectrometers include grating, prism-based, or interferometer-based spectrometers such as Fourier Transform Infrared, as well as optical detectors that do not discriminate an optical reading based on wavelength and which thus generate a signal indicative of the total energy across a portion of the optical spectrum. Such optical detectors include solid state semiconductor detectors, for example Silicon and InGaAs detectors, as well as photomultiplier tube (PMT) detectors. Suitable optical sources include solid state sources such as LEDs and lasers, and filament-based lamps and discharge lamps, many of which are available for generation of an optical signal within the UV, visible and infrared optical spectrum.

As described above, the minimum condition for use of this arrangement to collect a signal with the second group return optical fiber is that the shutter has a non-zero reflectance. Since this requirement is met by almost all practical materials the shutter may perform the desired optical calibration with no special requirements on the inner surface. Preferably the reflectance of the inner surface exceeds 1%, or exceeds 10%, or exceeds 50% at a predetermined wavelength within at least a first calibration wavelength interval.

As described above in relation to other aspects of the invention, the inner surface of the shutter may alternatively have a predetermined optical signature within at least a first calibration wavelength interval, wherein the predetermined optical signature is selected from the group: a diffuse reflectance spectrum, a specular reflectance spectrum, a Raman scattering spectrum, a fluorescence emission spectrum. Such alternatives may be used to improve the performance of the optical calibration. As described above, the open and closed states of the shutter, and also the presence of a particular type of connector may be determined based on the predetermined optical signature of the inner surface of the shutter by delivering light from optical source 829 to the inner surface 812 of the shutter via second group delivery optical fiber 831, and measuring the light collected from the inner surface of the shutter by second group return optical fiber 832 with spectrometer 830, or an optical detector in place of spectrometer 830, and comparing the collected light with the light expected, based on the predetermined optical signature. The particular type of the first group of one or more optical fibers that is being inserted into the first port may likewise be determined using this configuration by associating a specific optical signature with the ferrule or the first group of optical fibers as described above.

Figure 9:
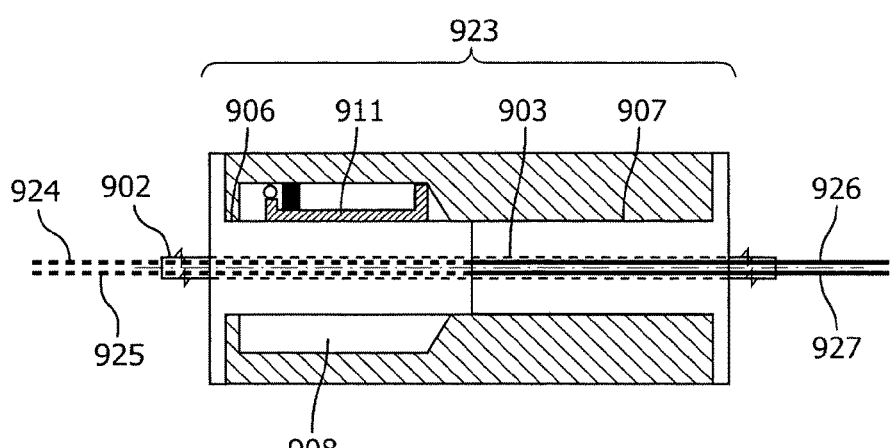
FIG. 9 illustrates an optical fiber connector arrangement 923 comprising an optical fiber connector, a second group of optical fibers 903 received within the second port 907 of the connector, and a first group of optical fibers 902 received within the first port 906 of the connector, wherein the shutter of the connector is in the open state 911.

FIG. 9 illustrates an optical fiber connector arrangement 923 comprising an optical fiber connector, a second group of optical fibers 903 received within a second port 907 of the connector, and a first group of optical fibers 902 received within a first port 906 of the connector, wherein the shutter of the connector is in the open state 911. The first group 902 is received within the first port 906 such that the first group at least partially fills the cavity 908. Furthermore the first group is arranged respective the second group such that each optical fiber (924, 925) in the first group 902 is in optical communication with one or more corresponding optical fibers (926, 927) in the second group 903. Corresponding optical fibers in the first group and the second group may be mated such that their end faces are touching, thus in a so-called butt-coupled arrangement, and are optionally furthermore axially pressed together by applying opposing axial forces along the axis of each optical fiber to ensure that reliable mating is achieved. Alternatively the end faces of the optical fibers may be separated by either an air gap or a positive lens, both of which help to reduce variations in transmission that are caused by misalignment of the optical fiber cores. In this configuration the shutter, being openable by applying a force to the outer surface of the shutter in a direction along the common axis allows the rapid conversion of the connector between a closed state in which dust or light is prevented from entering the connector, or in which an optical calibration or dark measurement can be carried out, and a connected state in which optical communication between corresponding optical fibers in the first and second groups is achieved. Advantageously this simple conversion can be carried out by a user with one hand, and without the need for a separate calibration surface, thereby improving workflow during a calibration procedure.

Figure 10:
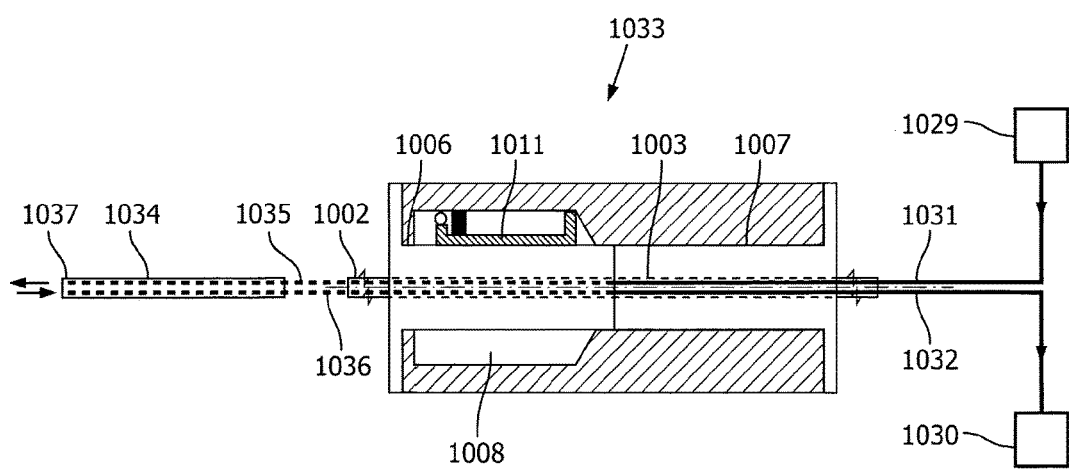
FIG. 10 illustrates an optical fiber connector arrangement 1033 comprising an optical fiber connector, a second group of optical fibers 1003 received within the second port 1007 of the connector, a first group of optical fibers 1002 received within the first port 1006 of the connector, an optical source 1029, a spectrometer 1030, and an optical probe 1034, wherein the shutter of the connector is in the open state 1011.

FIG. 10 illustrates an optical fiber connector arrangement 1033 comprising an optical fiber connector, a second group of optical fibers 1003 received within the second port 1007 of the connector, a first group of optical fibers 1002 received within the first port 1006 of the connector, an optical source 1029, a spectrometer 1030, and an optical probe 1034, wherein the shutter of the connector is in the open state 1011. The first group of one or more optical fibers 1002 at least partially fills the cavity 1008. Furthermore, the first group of one or more optical fibers is arranged respective the second group such that each optical fiber in the first group 1002 is in optical communication with one or more corresponding optical fibers in the second group 1003. The first group 1002 includes a first group delivery optical fiber 1035 and a first group return optical fiber 1036, and the second group 1003 includes a second group delivery optical fiber 1031 and a second group return optical fiber 1032. The first group delivery optical fiber and the first group return optical fiber each have a distal end located at the distal end 1037 of the optical probe 1034. Furthermore, the second group delivery optical fiber 1031 and the first group delivery optical fiber 1035 form an optical path between the optical source 1029 and the distal end 1037 of the optical probe 1034. Also, the first group return optical fiber 1036 and the second group return optical fiber 1032 form an optical path between the distal end 1037 of the optical probe 1034 and the spectrometer 1030. The arrangement may be used to perform optical measurements at the distal end of the optical probe. The optical probe may be any optical probe such as a probe used to inspect material properties or to measure the optical properties of a surface. Examples of suitable optical probes in the medical field include a needle, a cutting tool such as a surgical knife, a tissue bonding tool. Whilst two separate optical fibers are illustrated in FIG. 10 for performing the delivery and return of the optical light from the optical source, these functions may alternatively be combined into a single optical fiber, or their functionality distributed across a plurality of optical fibers.

With reference to FIG. 10, in a preferred configuration the second group delivery optical fiber 1031 has the same core diameter and numerical aperture as the first group delivery optical fiber 1035, and the second group return optical fiber 1032 has the same core diameter and numerical aperture as the first group return optical fiber 1036. However, by arranging that at least one of the following is true, the alignment tolerance between the first group 1003 and the second group 1002 is relaxed i) the second group delivery optical fiber (1031) has a numerical aperture (NA2D) that exceeds the first group delivery optical fiber (1035) numerical aperture (NA1D), or ii) the second group delivery optical fiber (1031) has a core diameter (D2D) that exceeds the first group delivery optical fiber (1035) core diameter (0), or iii) the second group return optical fiber (1032) has a numerical aperture (NA2R) that exceeds the first group return optical fiber (1036) numerical aperture (NA1R), or iv) the second group return optical fiber (1032) has core diameter (D2R) that exceeds the first group return optical fiber (1036) core diameter (D1R). By the term "exceeds" it is meant here that the ratio of the two parameters is preferably 1.1 or more, or 1.2 or more, or 1.5 or more. This principle applies in an analogous way to the arrangement of FIG. 9.

The numerical aperture defines the cone angle of both the beam of light emitted by an optical fiber, and the cone angle of the sensitivity of an optical fiber. It may be adjusted by adjusting the refractive index of the core and the cladding of the optical fiber. By arranging that the cone angle of at least one optical fiber in the connector on the second group side, exceeds that of a corresponding optical fiber on the first group side with which it communicates, the alignment tolerance of the first group respective the second group is relaxed. This advantageously permits the use of cheaper materials such as plastics on the side of the connector on the first group side, thereby making this side of the connector more suitable for use as a disposable part. Likewise by arranging that the core diameter of the second group delivery or return optical fiber exceeds that of the first group delivery or return optical fiber respectively, the alignment tolerance is relaxed. This arrangement is not limited to use in a specific field and may be used in any optical interconnection field such as telecommunications, and the optical test and measurement field. One example apparatus to which the first group may be connected is an optical probe, wherein the optical probe may be connected directly to the first group of one or more optical fibers to facilitate its disposal together with the first group, whereas a re-usable apparatus such as a measurement console may be connected to the second group of one or more optical fibers. Examples of suitable optical probes in the medical field include a needle, a cutting tool such as a surgical knife, a tissue bonding tool.

Various methods and computer program products are now disclosed in relation to the above optical fiber connector and connector arrangements.

A method of calibrating an optical fiber path is disclosed, the method including the steps of: measuring a reference optical spectrum (S1) with the spectrometer in the optical fiber connector arrangement of FIG. 8; measuring a signal optical spectrum (S2) with the spectrometer in the optical fiber connector arrangement of FIG. 10; and computing an adjusted optical spectrum (S3) based on either: i) the difference between the reference optical spectrum (S1) and the signal optical spectrum (S2), or ii) the ratio between the reference optical spectrum (S1) and the signal optical spectrum (S2), at one or more optical wavelengths within the spectral range detected by the spectrometer. The method may thus advantageously be used to calibrate the optical path of the first group of one or more optical fibers using the inner surface of the shutter as an optical reference surface, and to correct a subsequently measured signal optical spectrum that is measured with an optical probe. The method may for example be used to calibrate the transmission of the optical path.

Another computer program or computer program product is disclosed. This comprises instructions which when executed on a computer cause the computer to determine, based on the predetermined optical signature of the inner surface of the shutter whether the shutter in the optical fiber connector arrangement of FIG. 9 or FIG. 10 is in the open or closed state. The computer program or computer program product may compare the detected optical spectrum with a lookup table of spectra associated with specific shutter types in order to determine whether the connector or its open or closed stat, or its type.

Another computer program or computer program product is disclosed. This comprises instructions which when executed on a computer cause the computer to determine, based on the predetermined optical signature of the mating surface of first group of one or more optical fibers, or of the mating surface of a ferrule supporting the first group of one or more optical fibers, which type of first group of one or more optical fibers from a plurality of types of first group of one or more optical fibers associated with a predetermined optical signature, is in the cavity of the optical fiber connector. A lookup table may store the association between each type of first group of one or more optical fibers and its predetermined optical signature. The lookup table may be consulted during the determination process. This computer program or computer program product may be used with the arrangement of FIG. 9 or FIG. 10.

Another computer program or computer program product is disclosed. This comprises instructions which when executed on a computer cause the computer to generate either: i) a reference optical spectrum S1 with the optical fiber connector arrangement of FIG. 8, or to ii) to generate a signal optical spectrum S2 with the spectrometer in the optical fiber connector arrangement of FIG. 10. The computer program or computer program product thus permits the automatic acquisition of a spectrum based on the closed or open status of the shutter. Subsequent analysis of the spectra may be used to either interpret the type or nature of the material at the distal end of an optical probe, or to correct the signal optical spectrum based on the reference optical spectrum.

Another computer program or computer program product is disclosed. This comprises instructions which when executed on a computer cause the computer to perform the following steps: identify, based on the predetermined optical signature of the inner surface of the shutter, whether the shutter of the optical connector arrangement of FIG. 8 is in the closed state; measure a reference optical spectrum (S1) with the spectrometer in the optical fiber connector arrangement of FIG. 8 when the shutter is in the closed state; identify, based on the predetermined optical signature of the inner surface of the shutter, whether the shutter of the optical connector arrangement of FIG. 10 is in the open state; and to measure a signal optical spectrum (S2) with the spectrometer in the optical fiber connector arrangement of FIG. 10 when the shutter is in the open state; and to compute an adjusted optical spectrum (S3) based on either: i) the difference between the reference optical spectrum (S1) and the signal optical spectrum (S2), or ii) the ratio between the reference optical spectrum (S1) and the signal optical spectrum (S2) at one or more optical wavelengths within the spectral range detected by the spectrometer; wherein each of the above steps are performed in relation to the same optical fiber connector. The computer program or computer program product may thus advantageously automatically measure a reference spectrum and a signal optical spectrum based on the closed or open status of the shutter, and to use the reference spectrum to re-compute the signal optical spectrum, thereby improving the accuracy of the measured spectrum. Advantageously workflow is improved since an operator simply needs to remove the first group of one or more optical fibers from the connector in order to perform a calibration, and connect the first group to perform a signal measurement.

In accordance with another aspect of the invention various configurations of optical fiber connectors having corresponding alignment holes and alignment pins are provided which facilitate the mating of optical fiber connectors with improved repeatability.

Figure 11:
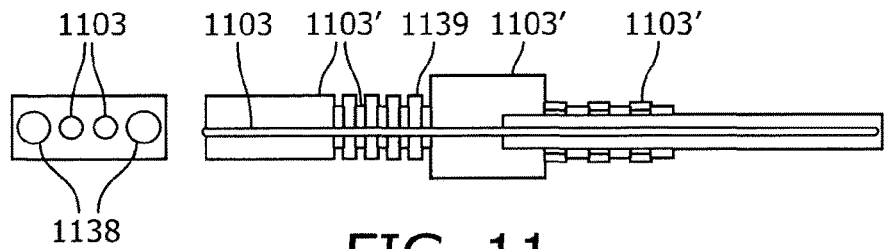
FIG. 11 illustrates an embodiment of a ferrule 1103' for supporting a group of one or more optical fibers 1103.

FIG. 11 illustrates an embodiment of a ferrule 1103' for supporting a group of one or more optical fibers 1103. The ferrule may be used to support the optical fibers such that they may be inserted into the first or second port 106, 107 of the optical fiber connector in FIG. 1. Ferrule 1103' may be formed from a moulded plastic for example. The optical fibers may be secured into the ferrule with epoxy, for example, or another adhesive. Ferrule 1103' includes an optional spring portion 1139 which when compressed provides an axial force along the axis of the ferrule in order to maintain good contact between abutting ferrules. Axial spring portion 1139 may for example be molded into the ferrule itself, or provided by a separate spring. Ferrule 1103' includes optional alignment holes 1138 which mate with complementary alignment pins in a corresponding ferrule such that an optical interconnection is formed within optical fiber connector 101 of FIG. 1. These alignment features improve the alignment accuracy of the corresponding optical fibers when mated. Two identical alignment features are shown in FIG. 11; however the alignment features may have different shapes or be positioned at different distances from the centerline of the ferrule in order to ensure that the connector can only be connected to a mating part in one orientation.

Figure 12:
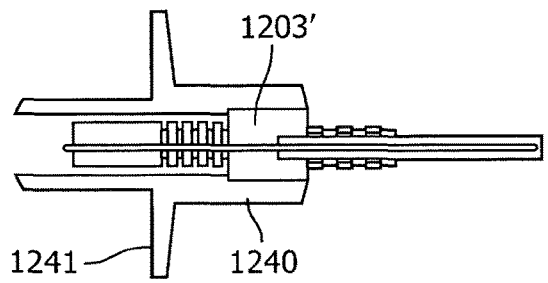
FIG. 12 illustrates another embodiment of a ferrule 1203' having a ferrule housing 1240.

FIG. 12 illustrates another embodiment of a ferrule 1203' having a ferrule housing 1240. The ferrule of FIG. 12 may be used to mate with the ferrule of FIG. 11. Optional ferrule housing 1240 includes a ferrule housing portion that extends beyond the end face of the optical fibers in order to protect them during insertion into the first port via the shutter of the optical fiber connector in FIG. 1. Housing 2140 in FIG. 12 includes optional shield 1241 for improving grip and presenting a physical barrier to contact between a gloved hand holding ferrule 1203' and a gloved hand holding corresponding ferrule 1203', thereby reducing the risk of medical contamination between the two ferrules.

Figure 13:
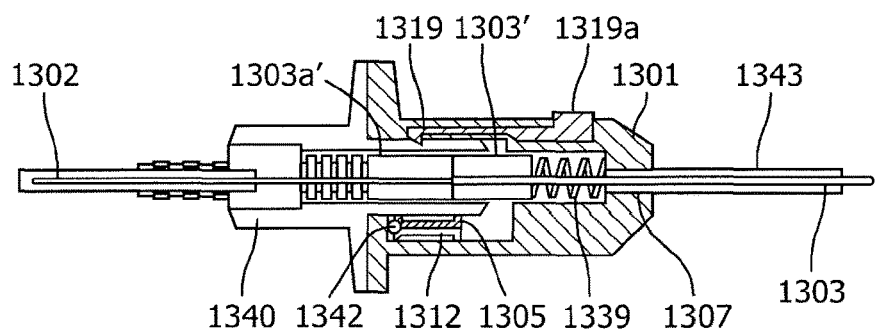
FIG. 13 illustrates an optical fiber connector assembly comprising optical fiber connector 1301, first group of one or more optical fibers 1302 and second group of one or more optical fibers 1303.

FIG. 13 illustrates an optical fiber connector assembly comprising optical fiber connector 1301, first group of one or more optical fibers 1302 and second group of one or more optical fibers 1303. Connector 1301 includes a shutter 1305 which in mounted to the body of the connector via hinge 1342. The inner surface of the shutter 1305 includes a white reference surface 1312 for calibrating the first group of optical fibers 1303 received within second port 1307. Ferrules 1303', 1303a' support the optical fibers in the second and first groups respectively, and axial spring portion 1339 provides an axial force to maintain good contact between the mating surfaces of the corresponding optical fibers. Optional second retaining means provided by snap-action catch 1319 is releasably secured via catch lever 1319a, and is used to temporarily connect housing 1340 of the first group of optical fibers 1302 to second group 1303 in order to effect optical communication therebetween. Optional strain relief 1343 relieves the strain on the optical fibers as they exit the second port 1307. Thus, the arrangement illustrated in FIG. 13 can be used to connect one or more optical fibers together.

Figure 14:
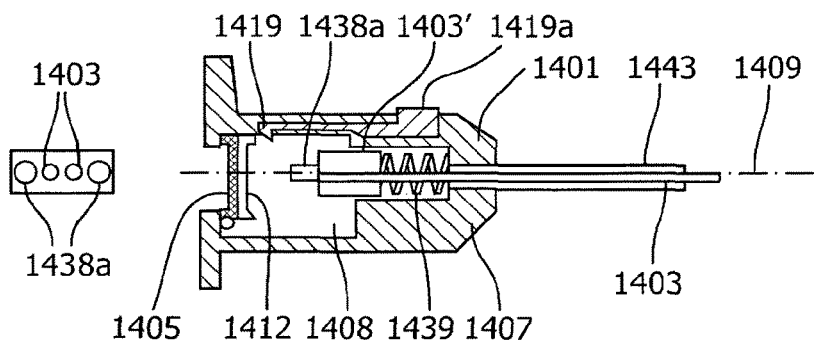
FIG. 14 illustrates another optical fiber connector assembly comprising optical fiber connector 1401 and second group of one or more optical fibers 1403.

FIG. 14 illustrates another optical fiber connector assembly comprising optical fiber connector 1401 and second group of one or more optical fibers 1403. Optional alignment pins 1438a, optional axial spring 1439, optional strain relief 1443, optional snap-action catch 1419 and catch release lever 1419a are also shown. Shutter 1405 of connector 1401 is in the closed state such that white reference surface 1412 lies in a plane that transversely intersects a common axis 1409 shared by the first and second port. The arrangement of FIG. 14 may thus be used to calibrate the optical transmission of the second group of one or more optical fibers 1403 by causing one or more of these optical fibers to emit light into cavity 1408, some of which will, consequent to the orientation of white reference surface 1412, be scattered back into the second group of one or more optical fibers 1403. The transmission of the second group of one or more optical fibers may thus be determined by comparing the power or the spectrum of the light inserted into the delivery optical fiber with that collected by the return optical fiber.

Optionally the shutter may be closed by a spring in order to form a light-tight enclosure within the connector and thereby permit a dark spectrum or a dark current measurement. In one example implementation the optical reference surface is formed from Spectralon and has a thickness of 5 mm to provide a reproducible and accurate white reference surface. The interior surface of the shutter may alternatively include an optical reference surface having a predetermined optical signature as described above. Optionally the shutter is configured to open such that when opened fully there is an air gap between the optical reference surface and the adjacent inner wall of the optical connector facing the shutter such that the optical reference surface is not damaged when opened. Workflow is improved in the present invention by the provision of an optical fiber connector having a shutter, which when closed provides a light-sealed environment within which dark reference measurements can be performed when the optical source is switched off, and which can be used for white reference measurements when the optical source is switched on. This facilitates an automatic white reference calibration and the automatic confirmation of when a specific optical cable is connected to the optical path. By integrating the optical reference surface into the connector, workflow is improved because a calibration procedure does not require a separate optical reference component. Furthermore, a more reliable optical calibration is achieved by re-using the same optical reference surface for each calibration procedure. The optional asymmetric design of the mating configuration of the optical fibers in the connector prevents erroneous connection of the optical probe. The present invention improves workflow by integrating a white reference into the connector and while simultaneously decreasing the cost by reducing the alignment requirements on the illumination fibers. In some applications ferrule 1303' in FIG. 13 may be a re-usable part and formed from a highly durable material such as ceramic or stainless steel for example, whereas mating ferrule 1303a' may be connected to a disposable optical probe such as a photonic needle, the disposable ferrule 1303a' being formed from a plastic ferrule in order to improve the durability and reduce the cost of the disposable portion of the connector. One of the main cost drivers for connectors in general is the tolerances that need to be achieved in order to obtain optimal alignment of the optical faces of the fibers that touch at the connector. Any concentricity errors of the fibers where they touch one another increases attenuation and may result in deviations from the spectral transmission if light is no longer inserted directly from the core, but instead reflects through the cladding onto the buffer and then is re-inserted into the core. In the latter case, the 'color' of the buffer will become visible in the connector's optical transmission spectrum. Because the color of the buffer is often not stable across batches of optical fibers, and because the amount of buffer color inserted into the light is dependent on the amount of light transmitted via the cladding compared to the amount of light transmitted via the core, this can affect the transmission spectrum itself.

In order to reduce the spectral instability and reduce the attenuation through misalignment, the illumination fiber and the detection fiber in the system cable may be oversized with an amount equal to the worst case tolerances that can be expected in the moulding and assembly process.

In the illumination or delivery optical fiber, oversizing requires the light source to transmit light from a second group delivery optical fiber into a first group delivery optical fiber, wherein the originating second group delivery optical fiber has a larger diameter. A common optical source used in optical sensing application is a halogen light source having a filament. Because the size of the filament of a tungsten halogen light source is typically larger than the diameter of the fiber, increasing the size of this second group delivery optical fiber respective to that of the first group delivery optical fiber has beneficial effects on the amount of light inserted into the second group delivery optical fiber. For example a 400 micron core diameter second group delivery optical fiber may be used in this way to couple light from a halogen source into a smaller, 200 micron core diameter first group delivery optical fiber. The fiber will however also insert light into the cladding because the core of the system cable illumination fiber always fully overlaps the cladding of the optical insert fiber.

In order to prevent light inserted into the cladding from affecting the spectrum in the illumination fiber, an epoxy based glue may optionally be used to glue the connector into a glass-filled moulded plastic ferrule. Providing the epoxy has a higher refractive index than both the cladding material and the core of the illumination fiber, the light leaking into the epoxy will not be guided back into the fiber. The glass-filled plastic of the ferrule scatters and absorbs the light that is reflected between cladding and epoxy. By the term "higher" it is meant here that the ratio of the two parameters is preferably 1.01 or more, or 1.02 or more, or 1.05 or more.

Figure 15:
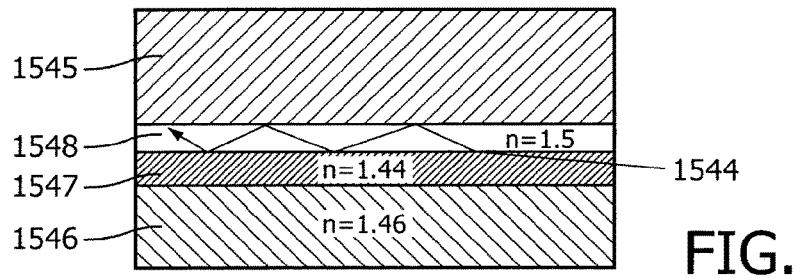
FIG. 15 illustrates a ray path 1544 within an optical fiber passing through a ferrule portion 1545.

FIG. 15 illustrates a ray path 1544 within an optical fiber passing through a ferrule portion 1545. Thus in FIG. 15, ray path 1544 indicative of light having escaped from fiber core 1546 with refractive index n=1.46 and which travels within the optical fiber cladding 1547 is guided into the epoxy layer 1548 where it is attenuated. Thus, FIG. 15 is illustrative of the principle of using an epoxy having a higher refractive index than that of the cladding to secure the optical fiber into the ferrule, and to simultaneously cause light to leak away from the cladding and thereby prevent cladding light from coupling into a mating optical fiber. The same principle may also be used in the return optical fiber path to relax its alignment tolerance.

Figure 16:
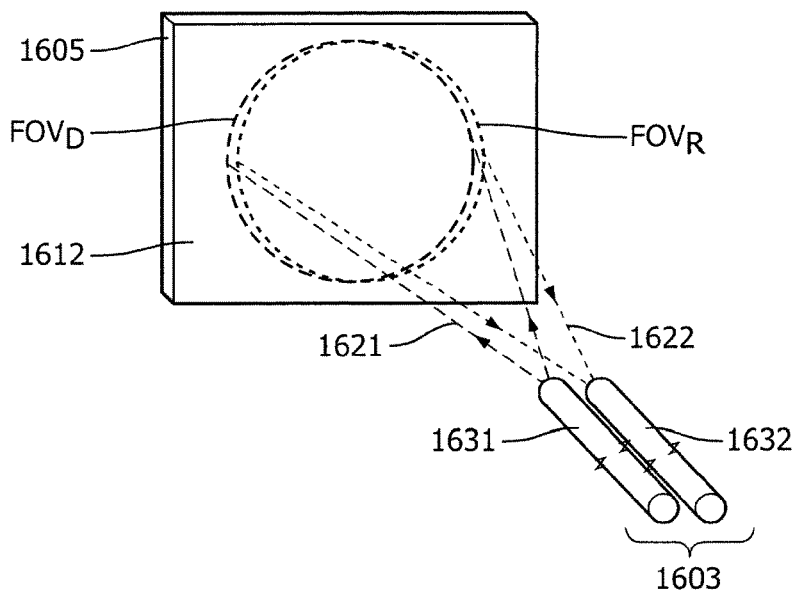
FIG. 16 illustrates an assembly of optical fibers 1603 respective the inner surface 1612 of a shutter 1605 that is in the closed state in which a second group delivery optical fiber 1631 has a delivery optical fiber field of view $FOV_D$ that overlaps with the field of view $FOV_R$ of a return optical fiber 1632 on the inner surface 1612 of the shutter 1605.
Figure 17:
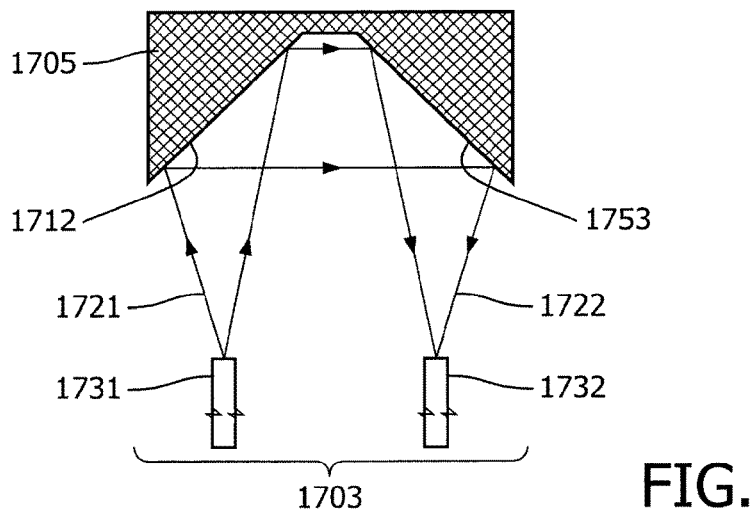
FIG. 17 illustrates an assembly of optical fibers 1703 respective the inner surface 1712 of a shutter 1705 that is in the closed state in which a beam redirector 1753 is positioned in the optical path between a second group delivery optical fiber 1731 and a second group return optical fiber 1732.

FIG. 16 illustrates an assembly of optical fibers 1603 respective the inner surface 1612 of a shutter 1605 that is in the closed state in which a second group delivery optical fiber 1631 has a delivery optical fiber field of view $FOV_D$ that overlaps with the field of view $FOV_R$ of a return optical fiber 1632 on the inner surface 1612 of the shutter 1605. FIG. 16 illustrates in more detail the relative orientations of the optical fibers in the second group 103 of FIG. 1, in particular showing the overlap of the fields of view of these optical fibers when the shutter is in the closed state. The field of view of the optical fibers is principally determined by the numerical aperture of each optical fiber, although additional optical components such as a lens or a beamstop may be positioned in the optical path of any of the optical fibers in the second group in order to further control the field of view. The overlap between the field of view $FOV_D$ of delivery optical fiber 1631 and the field of view $FOV_R$ of the return optical fiber 1632 ensures that at least a portion of the return light 1622 that is scattered or reflected or emitted by the inner surface 1612 of the shutter 1605 consequent to the emitted delivery light from delivery optical fiber 1631, is collected by the second group return optical fiber 1632. In other words, radiation, i.e. UV, visible or infrared light from the delivery optical fiber that is reflected or scattered by the inner surface of the shutter, or fluorescence emission light that is emitted by a layer of fluorescent material on the inner surface of the shutter, is thus collected by the return optical fiber 1632. Preferably there is a substantial overlap between $FOV_D$ and $FOV_R$ on the inner surface of the shutter, that is to say, on a plane that coincides with the inner surface of the shutter when the shutter is in the closed state, in order to optimize the amount of light collected by return optical fiber 1632. In so doing, the inner surface of the shutter may be used to calibrate the optical path between an optical source in communication with second group delivery optical fiber 1631, and an optical detector in optical communication with second group return optical fiber 1632. Preferably the overlap between $FOV_D$ and $FOV_R$ is such that 10% or more, or 20% or more, or 50% or more, or 75% or more, or 90% or more of the power emitted by delivery optical fiber 1631 falls within the spatial extent of the Full Width Half Maximum (FWHM) of the power sensitivity profile of the second group return optical fiber 1632 on the inner surface 1612 of the shutter. The overlap maybe controlled through the lateral separation of the optical fibers 1631, 1632 in FIG. 16. In FIG. 16, optical fibers 1631 and 1632 are adjacent to one another and touching each other in order to achieve a high degree of overlap of the respective field of view. In another configuration the optical fibers may have an increased lateral spacing in order to provide more design freedom whilst at the same time ensuring that a large proportion of the light emitted by optical fiber 1631 is collected by return optical fiber 1632. FIG. 17 is one such configuration having increased lateral spacing. In another configuration not shown in the Figures, the optical fibers may be mutually oriented such that projections of the optical axes of each optical fiber intersect on the inner surface of the shutter in order to improve the amount of light coupling between the delivery optical fiber 1631 and the return optical fiber 1632.

FIG. 17 illustrates an assembly of optical fibers 1703 respective the inner surface 1712 of a shutter 1705 that is in the closed state in which a beam redirector 1753 is positioned in the optical path between a second group delivery optical fiber 1731 and a second group return optical fiber 1732. In operation, delivery light 1721 from optical fiber 1731 is incident on the inner surface of the shutter 1712. Return light 1722 that is scattered or reflected or emitted by the inner surface 1712 of the shutter 1705 consequent to the emitted delivery light is redirected by the beam redirector 1753 towards the second group return optical fiber 1732 such that at least a portion of the return light is collected by the second group return optical fiber 1732. In so doing a wider separation between the optical fibers may be used. This relaxes the alignment tolerance of the second group optical fibers 1703. In alternative configurations, the positions of the optical fibers may be reversed, thus incident light 1731 may be first incident on a beam redirector. Beam redirector 1753 may be for example a flat surface, a convex or concave curved surface, and may additionally be a mirrored surface, a specular reflecting surface, a scattering surface, or a prism. Such may be used to control, or improve the amount of light collected by second group return optical fiber 1732 consequent to the emitted delivery light. Moreover additional beam redirectors may be used, for example on the portion of the inner surface of the shutter between inner surface portion 1712 and beam redirector 1753 to further control or improve the amount of light collected by second group return optical fiber 1732 consequent to the emitted delivery light. Inner surface 1712 may have a predetermined spectral signature, and may be for example a white reference surface, wherein the inner surface of the shutter may be formed from or include a layer of PTFE, Spectralon®, barium sulphate, or titanium dioxide, or the inner surface may be a wavelength calibration surface. As with FIG. 16, the embodiment of FIG. 17 may likewise be used to calibrate the optical path between an optical source in communication with delivery optical fiber 1631, and an optical detector in optical communication with second group return optical fiber 1632.

Figure 18:
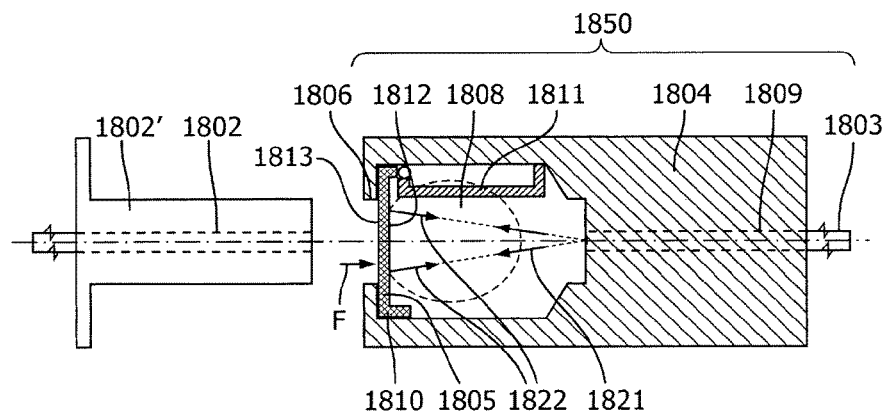
FIG. 18 illustrates an optical fiber connector assembly 1850 in which the shutter 1805 of the optical fiber connector assembly is in the closed state 1810, together with a separate first group of one or more optical fibers 1802.

The embodiment of FIG. 18 illustrates the collection of return light 1822 by a second group return optical fiber in the second group 1803 that is scattered or reflected or emitted by the inner surface 1812 of the shutter 1805 consequent to delivery light emitted by a delivery optical fiber in the second group 1803.

Figure 19:
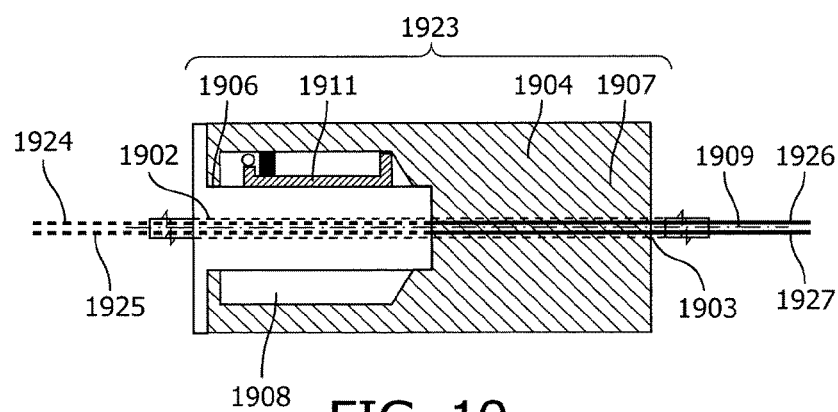
FIG. 19 illustrates an optical fiber connector arrangement 1923 comprising an optical fiber connector assembly, and a first group of optical fibers 1902 received within the first port 1906 of the optical fiber connector assembly, wherein the shutter of the optical fiber connector assembly is in the open state 1911.

The embodiment of FIG. 19 illustrates the optical connection between optical fibers 1924 and 1925 in first group of optical fibers 1902 received within the first port 1906 of the optical fiber connector assembly, and corresponding optical fibers 1926 and 1927 in second group of optical fibers 1903 wherein the shutter of the optical fiber connector assembly is in the open state 1911.

Figure 20:
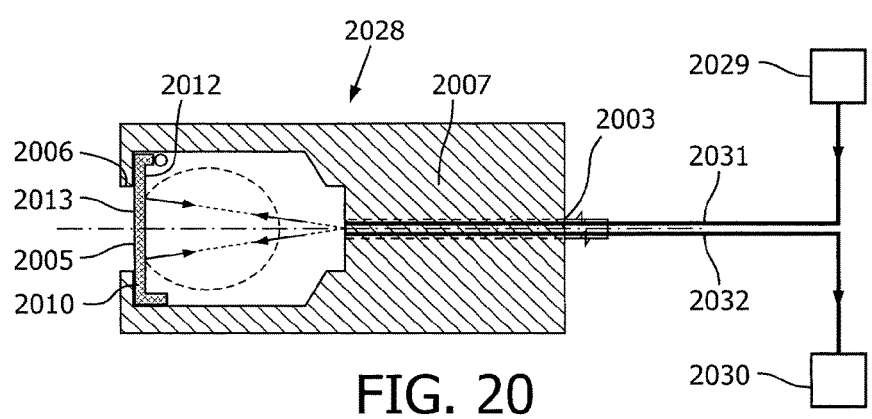
FIG. 20 illustrates an optical fiber connector arrangement 2028 comprising an optical fiber connector assembly, an optical source 2029 and a spectrometer 2030, wherein the shutter 2005 of the connector is in the closed state 2010.

The embodiment of FIG. 20 may be used to perform an optical calibration of the optical fiber path between optical source 2029 and spectrometer 2030 In the same manner as described in relation to FIG. 8.

Figure 21:
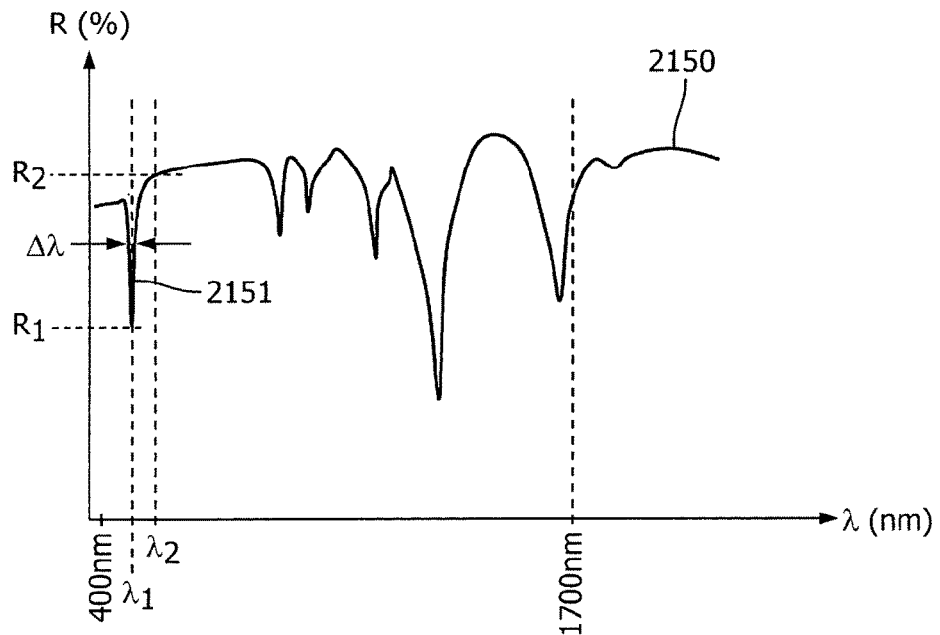
FIG. 21 illustrates an exemplary predetermined optical signature of the inner surface of a shutter that may be used to perform a wavelength calibration of an optical source.

FIG. 21 illustrates an exemplary predetermined optical signature of the inner surface of a shutter that may be used to perform a wavelength calibration of an optical source. The predetermined optical signature may be a property of the inner surface of the shutter used throughout this application, exemplarily in the configuration of FIGS. 10 and 20, wherein the characteristic peak or trough 2151 of the predetermined optical signature 2150 provides a reference wavelength against which to calibrate the optical source 1029, 2029 or the optical detector 1030, 2030. In the example of FIG. 21 the predetermined optical signature is a diffuse reflectance spectrum and the spectrum is provided by Dysprosium oxide-doped Spectralon® wavelength calibration standard supplied by Labsphere, North Sutton N.H., USA. Other wavelength calibration standards may alternatively be used, such as a fluorescence emission standard, or a reflectance standard. The horizontal axis in FIG. 21 represents the wavelength in nanometers and the vertical axis represents the diffuse reflectance. The diffuse reflectance 2150 illustrated in FIG. 21 has a trough 2151 at wavelength $\lambda_1$ within a calibration wavelength interval of 400 nm to 1700 nm with a spectral full width half maximum $\Delta\lambda$. Preferably $\Delta\lambda$ is less than or equal to 20 nm, more preferably, less than or equal to 10 nm, or 5 nm. Narrowing the window of $\Delta\lambda$ provides improved accuracy of the wavelength calibration. The calibration wavelength interval 400 nm to 1700 nm represents a useful portion of the spectral transmission window of conventional optical fibers. Furthermore the difference between the value $R_1$ of the diffuse reflectance at the trough wavelength at 2151, $\lambda_1$ and the diffuse reflectance at a reference value $R_2$ at wavelength $\lambda_2$ that is adjacent to the peak or trough is preferably greater than or equal to 10%. Increasing the difference between $R_2$ and $R_1$ to for example greater than or equal to 20%, or greater than or equal to 50% further improves the accuracy of the wavelength calibration. When used in the embodiment of FIG. 19, the predetermined optical signature of FIG. 21 may be used to provide a predetermined reference wavelength that can be used to calibrate the optical source or the optical detector.

Figure 22:
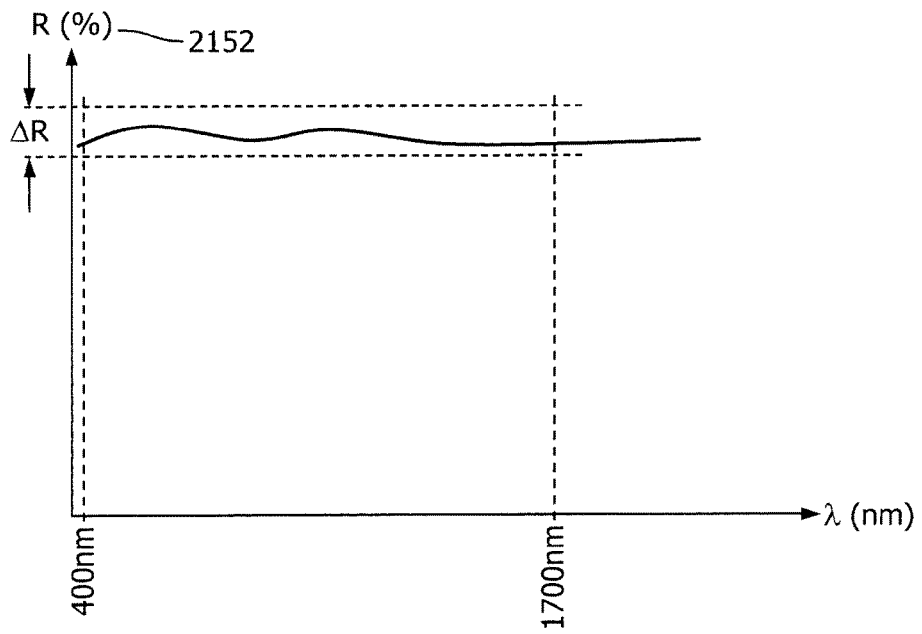
FIG. 22 illustrates an exemplary predetermined optical signature of the inner surface of a shutter that may be used to calibrate the transmission of an optical fiber.

FIG. 22 illustrates an exemplary predetermined optical signature of the inner surface of a shutter that may be used to calibrate the transmission of an optical fiber. The exemplary predetermined optical signature in FIG. 22 is a diffuse reflectance spectrum which is substantially constant across the wavelength interval 400 nm to 1700 nm. By providing a predetermined, or preferably substantially constant, reflectance across this calibration wavelength interval, the predetermined optical signature may be used to calibrate the optical transmission of the second group delivery optical fiber 2031 and the second group return optical fiber 2032 using the configuration of FIG. 20. The predetermined optical signature may be provided by for example a PTFE layer, or a Spectralon® layer, or a barium sulphate layer, or a titanium dioxide layer as described hereinbefore. Preferably the predetermined optical signature provided by the inner surface 112 of the shutter 105 has an average diffuse reflectance value that is greater than or equal to 90% within the calibration wavelength interval of 400 nm to 1700 nm and a variation in diffuse reflectance value $\Delta R$ that is less than or equal to 10% within the calibration wavelength interval of 400 nm to 1700 nm. Narrowing the variation in diffuse reflectance value $\Delta R$ to less than or equal to 5%, or to less than or equal to 1% further improves the accuracy of the calibration.

The invention is now described with reference to a number of Examples.

1$^{st}$ Example

An optical fiber connector (101) for mating a first group of one or more optical fibers (102) with one or more corresponding optical fibers in a second group of one or more optical fibers (103); the optical fiber connector comprising a body (104) and a shutter (105);

wherein the body (104) has a common axis (109), a cavity (108) disposed along the common axis (109), a first port (106) for receiving the first group of one or more optical fibers (102), and a second port (107) for receiving the second group of one or more optical fibers (103), wherein the first port (106) is at one end of the body (104) and extends along the common axis (109) into the cavity (108), and the second port (107) is at the opposite end of the body (104) and extends along the common axis (109) into the cavity (108);

wherein the shutter (105) is hingeably mounted to the first port; the shutter being selectively movable between a closed state (110) in which the shutter blocks the first port and in which the shutter lies in a plane that transversely intersects the common axis, and an open state (111) in which the shutter lies in a plane that forms an acute angle with the common axis; and wherein the shutter has an inner surface (112) that is innermost to the cavity, and an opposing outer surface (113);

wherein the shutter is movable between the closed state and the open state by applying a force (F) to the outer surface of the shutter in a direction along the common axis.

2$^{nd}$ Example

The optical fiber connector (101) according to Example 1 wherein the shutter (105) is movable between the closed state (110) and the open state such that the shutter is within the cavity in the open state (111).

3$^{rd}$ Example

The optical fiber connector according to Example 2 further comprising mechanically resistive means (414), the mechanically resistive means being in mechanical communication with the shutter and the body; wherein the mechanically resistive means is configured to provide a restoring force to counteract movement of the shutter from the closed state towards the open state.

4$^{th}$ Example

The optical fiber connector according to any one of Examples 1 to 3 wherein both the body and the shutter are opaque to optical wavelengths within at least a first calibration wavelength interval, and wherein the shutter blocks the first port in the closed state to form a light-impermeable barrier between the first port and the cavity; the light-impermeable barrier being opaque to optical wavelengths within the first calibration wavelength interval.

5$^{th}$ Example

The optical fiber connector according to any one of Examples 1 to 4 wherein the inner surface of the shutter has a predetermined optical signature within at least a first calibration wavelength interval, and wherein the predetermined optical signature is selected from the group: a diffuse reflectance spectrum, a specular reflectance spectrum, a Raman scattering spectrum, a fluorescence emission spectrum.

6$^{th}$ Example

The optical fiber connector according to Example 5 wherein the inner surface of the shutter is formed from PolyTetraFluoroEthylene material and the diffuse reflectance spectrum is provided by the PolyTetraFluoroEthylene material.

7$^{th}$ Example

The optical fiber connector according to any one of Examples 1 to 6 further comprising a debris collection zone (515); wherein the debris collection zone is disposed within the cavity and is formed from either a sticky surface or an electrostatically charged surface.

8$^{th}$ Example

An optical fiber connector arrangement (720) comprising the optical fiber connector of any one of Examples 1 to 7 and a second group of one or more optical fibers (703);

the second group of one or more optical fibers being received within the second port (707) such that when delivery light (721) emitted by the one or more optical fibers in the second group (703) into the cavity (708) is incident upon the inner surface (712) of the shutter (705) in the closed state (710), return light (722) that is scattered or reflected or emitted by the inner surface of the shutter consequent to the emitted delivery light is at least partially collected by the one or more optical fibers in the second group (703).

9$^{th}$ Example

An optical fiber connector arrangement (923) according to Example 8 wherein the shutter is in the open state (911), the optical fiber connector arrangement further including a first group of one or more optical fibers (902);

wherein the first group is received within the first port (906) such that the first group (902) at least partially fills the cavity (908);

the first group being arranged respective the second group such that each optical fiber (924, 925) in the first group (902) is in optical communication with one or more corresponding optical fibers (926, 927) in the second group (903).

10$^{th}$ Example

The optical fiber connector arrangement (828) according to Example 8 further comprising an optical source (829) and a spectrometer (830);

wherein the second group includes a second group delivery optical fiber (831) and a second group return optical fiber (832); wherein the second group delivery optical fiber (831) is in optical communication with the optical source (829) and wherein the second group return optical fiber (832) is in optical communication with the spectrometer (830);

and wherein the shutter (805) is in the closed state (810) such that the second group delivery optical fiber (831) and the second group return optical fiber (832) form an optical path between the source and the spectrometer that includes the inner surface (812) of the shutter (805).

11$^{th}$ Example

The optical fiber connector arrangement (1033) according to Example 9 further comprising an optical source (1029), a spectrometer (1030) and an optical probe (1034);

wherein the first group (1002) includes a first group delivery optical fiber (1035) and a first group return optical fiber (1036), and wherein the second group (1003) includes a second group delivery optical fiber (1031) and a second group return optical fiber (1032);

wherein the first group delivery optical fiber (1035) and the first group return optical fiber (1036) each have a distal end located at the distal end (1037) of the optical probe (1034); and wherein the second group delivery optical fiber (1031) and the first group delivery optical fiber (1035) form an optical path between the optical source (1029) and the distal end (1037) of the optical probe (1034);

and wherein the first group return optical fiber (1036) and the second group return optical fiber (1032) form an optical path between the distal end (1037) of the optical probe (1034) and the spectrometer (1030).

12$^{th}$ Example

An optical fiber connector arrangement (1033) according to Example 11 wherein at least one of the following:

i) the second group delivery optical fiber (1031) has a numerical aperture (NA2D) that exceeds the first group delivery optical fiber (1035) numerical aperture (NA1D), or ii) the second group delivery optical fiber (1031) has a core diameter (D2D) that exceeds the first group delivery optical fiber (1035) core diameter (D1D), or iii) the second group return optical fiber (1032) has a numerical aperture (NA2R) that exceeds the first group return optical fiber (1036) numerical aperture (NA1R), or iv) the second group return optical fiber (1032) has core diameter (D2R) that exceeds the first group return optical fiber (1036) core diameter (D1R).

13$^{th}$ Example

A method of calibrating an optical fiber path comprising the steps of:

measuring a reference optical spectrum (S1) with the spectrometer in the optical fiber connector arrangement (828) of Example 10;

measuring a signal optical spectrum (S2) with the spectrometer in the optical fiber connector arrangement (1033) of Example 11; and computing an adjusted optical spectrum (S3) based on either:

i) the difference between the reference optical spectrum (S1) and the signal optical spectrum (S2), or ii) the ratio between the reference optical spectrum (S1) and the signal optical spectrum (S2), at one or more optical wavelengths within the spectral range detected by the spectrometer.

14$^{th}$ Example

A computer program or computer program product comprising instructions which when executed on a computer cause the computer to generate either:

i) a reference optical spectrum with the optical fiber connector arrangement (828) of Example 10, or to ii) to generate a signal optical spectrum (S2) with the spectrometer in the optical fiber connector arrangement (1033) of Example 11.

15$^{th}$ Example

A computer program or computer program product comprising instructions which when executed on a computer cause the computer to perform the following steps:

identify, based on the predetermined optical signature of the inner surface of the shutter, whether the shutter of the optical connector arrangement (828) of Example 10 is in the closed state;

measure a reference optical spectrum (S1) with the spectrometer in the optical fiber connector arrangement (828) of Example 10 when the shutter is in the closed state;

identify, based on the predetermined optical signature of the inner surface of the shutter, whether the shutter of the optical connector arrangement (1033) of Example 11 is in the open state; and to measure a signal optical spectrum (S2) with the spectrometer in the optical fiber connector arrangement (1033) of Example 11 when the shutter is in the open state; and to compute an adjusted optical spectrum (S3) based on either:
  i) the difference between the reference optical spectrum (S1) and the signal optical spectrum (S2), or
  ii) the ratio between the reference optical spectrum (S1) and the signal optical spectrum (S2) at one or more optical wavelengths within the spectral range detected by the spectrometer;
wherein each of the above steps are performed in relation to the same optical fiber connector.

To summarize, an optical fiber connector for mating a first group of one or more optical fibers with one or more corresponding optical fibers in a second group of one or more optical fibers is disclosed. The optical fiber connector includes a shutter, which prevents the ingress of debris into the connector, and provides an optical reference surface with which to calibrate optical fibers that are inserted into the connector. The optical fiber connector finds particular application in the medical field wherein it may be used in the interconnection of optical fibers in a photonic needle application.

Whilst the invention has been illustrated and described in detail in the drawings and foregoing description, such illustrations and description are to be considered illustrative or exemplary and not restrictive; the invention is not limited to the disclosed embodiments and can be used for optically connecting optical fibers in various applications both in and beyond the medical field.

The invention claimed is:

1. An optical fiber connector assembly for mating a first group of optical fibers, comprising:
  a first group delivery optical fiber and a first group return optical fiber with corresponding optical fibers in a second group of optical fibers comprising a second group delivery optical fiber and a second group return optical fiber, the optical fiber connector assembly comprising: a body, comprising a common axis, a cavity disposed along the common axis, a first port for receiving the first group of optical fibers, the first port being disposed at one end of the body and extending along the common axis into the cavity, wherein the second group of optical fibers is arranged at the opposite end of the body such that each end face of the optical fibers in the second group of optical fibers face the cavity; and second group of optical fibers comprising a second group delivery optical fiber, and a second group return optical fiber and a shutter hingeably mounted to the first port, the shutter being selectively movable between a closed state in which the shutter blocks the first port and in which the shutter lies in a plane that transversely intersects the common axis, and an open state in which the shutter lies in a plane that forms an acute angle with the common axis; and
  wherein, the shutter has an inner surface that is innermost to the cavity, and an opposing outer surface; the shutter is movable between the closed state and the open state by applying a force (F) to the outer surface of the shutter in a direction along the common axis; the second group of optical fibers is further arranged such that when the shutter is in the closed state, delivery light emitted by the second group delivery optical fiber into the cavity is incident upon the inner surface of the shutter and return light that is scattered or reflected or emitted by the inner surface of the shutter consequent to the emitted delivery light is at least partially collected by the second group return optical fiber; both the body and the shutter are opaque to optical wavelengths within at least a first calibration wavelength interval, and wherein the shutter blocks the first port in the closed state to form a light-impermeable barrier between the first port and the cavity: the light-impermeable barrier being opaque to optical wavelengths within the first calibration wavelength interval.

2. The optical fiber connector assembly according to claim 1, wherein the shutter (105) is movable between the closed state (110) and the open state such that the shutter is within the cavity when the shutter (105) is in the open state (111).

3. The optical fiber connector according to claim 1, wherein the inner surface of the shutter has a predetermined optical signature within at least a first calibration wavelength interval, and wherein the predetermined optical signature is selected from the group: a diffuse reflectance spectrum, a specular reflectance spectrum, a Raman scattering spectrum, a fluorescence emission spectrum.

4. The optical fiber connector according to claim 3, wherein: the predetermined optical signature has at least one peak or at least one trough within the first calibration wavelength interval of 400 nm to 1700 nm; the at least one peak or at least one trough has a spectral full width half maximum ($\Delta\lambda$) of less than or equal to 20 nm; and a difference between a value ($R_1$) of the optical signature at the peak or trough and a reference value ($R_2$) of the optical signature at an adjacent wavelength ($\lambda_2$) to the peak or trough is greater than or equal to 10%.

5. The optical fiber connector assembly according to claim 1, wherein the inner surface of the shutter has an average diffuse reflectance value that is greater than or equal to 90% within a first calibration wavelength interval of 400 nm to 1700 nm and a variation in diffuse reflectance value ($\Delta R$) that is less than or equal to 10% within the first calibration wavelength interval of 400 nm to 1700 nm.

6. The optical fiber connector assembly according to claim 1, wherein the inner surface of the shutter comprises at least one beam redirector, wherein the beam redirector is positioned in an optical path between the second group delivery optical fiber and the second group return optical fiber when the shutter is in the closed state, such that when delivery light emitted by the second group delivery optical fiber irradiates the inner surface of the shutter, return light that is scattered or reflected or emitted by the inner surface of the shutter consequent to the emitted delivery light is redirected by the beam redirector towards the second group return optical fiber.

7. The optical fiber connector assembly according to claim 1 further comprising a debris collection zone, wherein the debris collection zone is disposed within the cavity and is formed from either a sticky surface or an electrostatically charged surface.

8. An optical fiber connector for mating a first group of optical fibers, comprising: a first group delivery optical fiber: and a first group return optical fiber with corresponding optical fibers in a second group of optical fibers comprising a second group delivery optical fiber and a second group return optical fiber, the optical fiber connector comprising: a body and a shutter the body comprising: a common axis, a cavity disposed along the common axis, a first port for receiving the first group of optical fibers, and a second port for receiving the second group of optical fibers, wherein the first port is at one end of the body and extends along the common axis into the cavity, and the second port is at the opposite end of the body and extends along the common axis into the cavity;

wherein: the shutter is hingeably mounted to the first port, the shutter being selectively movable between a closed state in which the shutter blocks the first port and in which the shutter lies in a plane that transversely intersects the common axis, and an open state in which the shutter lies in a plane that forms an acute angle with the common axis; the shutter has an inner surface that is innermost to the cavity, and an opposing outer surface; wherein the shutter is movable between the closed state and the open state by applying a force (F) to the outer surface of the shutter in a direction along the common axis; the second port is configured such that when the second group of optical fibers is received within the second port and the shutter is in the closed state, delivery light emitted by the second group delivery optical fiber into the cavity is incident upon the inner surface of the shutter and return light that is scattered or reflected or emitted by the inner surface of the shutter consequent to the emitted delivery light is at least partially collected by the second group return optical fiber: and both the body and the shutter are opaque to optical wavelengths within at least a first calibration wavelength interval, and wherein the shutter blocks the first port in the closed state to form a light-impermeable barrier between the first port and the cavity: the light-impermeable barrier being opaque to optical wavelengths within the first calibration wavelength interval.

9. An optical fiber connector arrangement comprising the optical fiber connector of claim 8, wherein a second group of optical fibers comprising a second group delivery optical fiber and a second group return optical fiber is received within the second port.

10. The optical fiber connector arrangement according to claim 9 wherein: the shutter is in the open state, the optical fiber connector arrangement further including a first group of one or more optical fibers; the first group is received within the first port such that the first group of optical fibers at least partially fills the cavity; and the first group is arranged respective the second group such that each optical fiber in the first group is in optical communication with one or more corresponding optical fibers in the second group.

11. The optical fiber connector arrangement according to claim 10, further comprising an optical source), a spectrometer and an optical probe; wherein the first group includes a first group delivery optical fiber and a first group return optical fiber;

wherein the first group delivery optical fiber and the first group return optical fiber each have a distal end located at the distal end of the optical probe;

and wherein the second group delivery optical fiber and the first group delivery optical fiber form an optical path between the optical source and the distal end of the optical probe;

and wherein the first group return optical fiber and the second group return optical fiber form an optical path between the distal end of the optical probe and the spectrometer.

12. The optical fiber connector arrangement according to claim 9, further comprising an optical source and a spectrometer;

wherein the second group delivery optical fiber is in optical communication with the optical source and wherein the second group return optical fiber is in optical communication with the spectrometer;

and wherein the shutter is in the closed state such that the second group delivery optical fiber and the second group return optical fiber form an optical path between the source and the spectrometer that includes the inner surface of the shutter.

13. A method of calibrating an optical fiber path, the method comprising:

measuring a reference optical spectrum with the spectrometer in the optical fiber connector arrangement of claim 12;

measuring a signal optical spectrum with the spectrometer in the optical fiber connector arrangement; and computing an adjusted optical spectrum based on either:
  i) a difference between the reference optical spectrum and the signal optical spectrum, or
  ii) a ratio between the reference optical spectrum and the signal optical spectrum, at one or more optical wavelengths within a spectral range detected by the spectrometer.

14. A non-transitory computer program or computer program product, comprising instructions, which when executed on a computer cause the computer to perform the following steps:

identify, based on a predetermined optical signature of the inner surface of the shutter, whether the shutter of the optical connector arrangement of claim 12 is in the closed state;

measure a reference optical spectrum with the spectrometer in the optical fiber connector arrangement when the shutter is in the closed state;

identify, based on the predetermined optical signature of the inner surface of the shutter, whether the shutter of the optical connector arrangement is in the open state; and to measure a signal optical spectrum with the spectrometer in the optical fiber connector arrangement when the shutter is in the open state; and to compute an adjusted optical spectrum based on either:
  i) a difference between the reference optical spectrum and the signal optical spectrum, or
  ii) a ratio between the reference optical spectrum and the signal optical spectrum at one or more optical wavelengths within a spectral range detected by the spectrometer;

wherein each of the steps is performed in relation to the same optical fiber connector.

* * * * *